(12) United States Patent
Herling et al.

(10) Patent No.: US 10,386,332 B2
(45) Date of Patent: Aug. 20, 2019

(54) FLUIDIC ANALYSIS AND SEPARATION

(71) Applicant: CAMBRIDGE ENTERPRISE LIMITED, Cambridge (GB)

(72) Inventors: Therese Herling, Cambridge (GB); Thomas Mueller, Cambridge (GB); Tuomas Knowles, Cambridge Cambridgeshire (GB)

(73) Assignee: Cambridge Enterprise Limited, Cambridge (GB)

( * ) Notice: Subject to any disclaimer, the term of this patent is extended or adjusted under 35 U.S.C. 154(b) by 148 days.

(21) Appl. No.: 15/307,221

(22) PCT Filed: Apr. 30, 2015

(86) PCT No.: PCT/GB2015/051256
§ 371 (c)(1),
(2) Date: Oct. 27, 2016

(87) PCT Pub. No.: WO2015/166247
PCT Pub. Date: Nov. 5, 2015

(65) Prior Publication Data
US 2017/0052147 A1    Feb. 23, 2017

(30) Foreign Application Priority Data
Apr. 30, 2014   (GB) .................................. 1407641.8

(51) Int. Cl.
*G01N 27/447*     (2006.01)
*B01L 3/00*       (2006.01)
*G01N 15/02*      (2006.01)

(52) U.S. Cl.
CPC .... *G01N 27/44795* (2013.01); *B01L 3/50273* (2013.01); *B01L 3/502715* (2013.01);
(Continued)

(58) Field of Classification Search
CPC ..... B01L 2400/0451; B01L 2400/0421; G01N 27/447; G01N 27/44704; G01N 27/44743;
(Continued)

(56) References Cited

U.S. PATENT DOCUMENTS 5,503,723 A * 4/1996 Ruddy ................... A61K 9/146
                                                        204/450
5,932,100 A * 8/1999 Yager ................. B01D 11/0492
                                                        210/511

(Continued)

FOREIGN PATENT DOCUMENTS

WO      03066191       8/2003
WO     2006037561      4/2006
WO     2014064438      5/2014

OTHER PUBLICATIONS

International Search Report for PCT/GB2015/051256, Completed by the European Patent Office on Aug. 17, 2015, All together 3 pages.
(Continued)

*Primary Examiner* — Alexander S Noguerola
(74) *Attorney, Agent, or Firm* — Wolf, Greenfield & Sacks, P.C.

(57) ABSTRACT

A method for analyzing a component is provided. The method includes the steps of: (iii) providing the electrophoretic or thermophoretic movement of the component into a second fluid flow; (iv) diverting a part of a first fluid flow, a part of the second fluid flow, or parts of the first fluid flow and the second fluid flow, wherein the diverted part is a third fluid flow which includes, the component; (v) contacting the third fluid flow with a fourth fluid flow, such as to form a laminar flow; (vi) providing the diffusion of the component into the fourth fluid flows.

24 Claims, 5 Drawing Sheets

(52) U.S. Cl.
CPC .. *B01L 3/502776* (2013.01); *G01N 27/44756* (2013.01); *G01N 27/44769* (2013.01); *G01N 27/44791* (2013.01); *B01L 2200/0652* (2013.01); *B01L 2300/0645* (2013.01); *B01L 2300/0861* (2013.01); *B01L 2300/0864* (2013.01); *B01L 2300/0883* (2013.01); *B01L 2400/0421* (2013.01); *B01L 2400/0451* (2013.01); *B01L 2400/0472* (2013.01); *G01N 15/0266* (2013.01)

(58) Field of Classification Search
CPC ....... G01N 27/44756; G01N 27/44765; G01N 27/453
See application file for complete search history.

(56) References Cited

U.S. PATENT DOCUMENTS

| | | | | |
|---|---|---|---|---|
| 6,432,630 | B1* | 8/2002 | Blankenstein | B01D 57/02 422/186 |
| 8,679,313 | B2* | 3/2014 | Fiering | G01N 27/44769 204/459 |
| 2005/0121604 | A1 | 7/2005 | Mueth et al. | |
| 2006/0263903 | A1 | 11/2006 | Chien | |
| 2008/0037044 | A1 | 2/2008 | Tse et al. | |
| 2011/0264380 | A1 | 10/2011 | Cottet et al. | |
| 2016/0266138 | A1 | 9/2016 | Yates et al. | |

OTHER PUBLICATIONS

Kamholz and Yager Biophyiscal Journal 2001, vol. 80, No. 1, pp. 155-160, "Theoretical Analysis of Molecular Diffusion in Pressure-Driven Laminar Flow in Microfluidic Channels".

Kamholz et al. Biophyiscal Journal 2001, vol. 80, No. 4, pp. 1967-1972, "Optical Measurement of Transverse Molecular Diffusion in a Microchannel".

Hatch et al. Nature Biotechnology May 2001, vol. 19, No. 5, pp. 461-465, "A rapid diffusion immunoassay in a T-sensor".

Herling et al. Applied Physics Letters 2013, vol. 102, pp. 184102-184104, "Integration and characterization of solid wall electrodes in microfluidic devices fabricated in a single photolithography step".

Jacobson et al. Analytical Chemistry Oct. 15, 1994, vol. 66, No. 20, pp. 3472-3476, "Microchip Capillary Electrophoresis with an Integrated Postcolumn Reactor".

Jacobson et al. Analytical Chemistry Dec. 1, 1994, vol. 66, No. 23, pp. 4127-4132, "Precolumn Reactions with Electrophoretic Analysis Integrated on a Microchip".

Kohlheyer et al. Eletrophoresis 2008, vol. 29, pp. 977-993, "Miniaturizing free-flow electrophoresis—a critical review".

Liu et al. Analytical Chemistry Oct. 1, 2000, vol. 72, No. 19, pp. 4608-4613, "Electrophoretic Separation of Proteins on a Microchip with Noncovalent, Postcolumn Labeling".

McDonald et al. Accounts of Chemical Research 2002, vol. 35, No. 7, pp. 491-499, "Poly(dimethylsiloxane) as a Material for Fabricating Microfluidic Devices".

Tan et al. Biomircofluidics 2010 vol. 4, pp. 032204-1-032204-8, "Oxygen plasma treatment for reducing hydrophobicity of a sealed polydimethylsiloxane microchannel".

Wales et al. J.Phys. Chem. A 1997, vol. 101, No. 28, pp. 5111-5116, "Global Optimization by Basin-Hopping and the Lowest Energy Structures of Lennard-Jones Clusters Containing up to 110 Atoms".

* cited by examiner

Figures 5 (a)-(d)
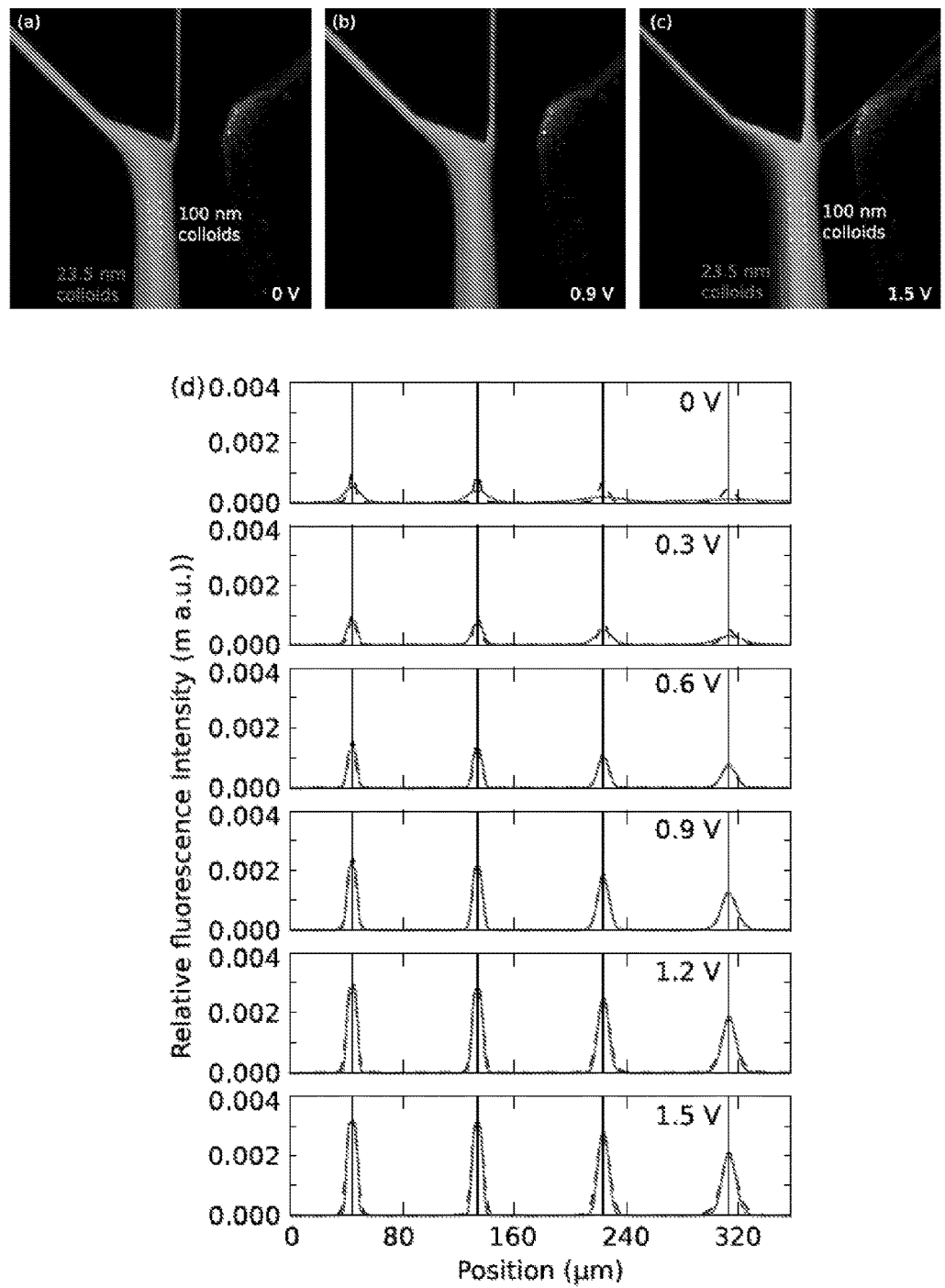

FLUIDIC ANALYSIS AND SEPARATION

CROSS-REFERENCE TO RELATED APPLICATION

This application is the U.S. national phase of PCT Application No. PCT/GB2015/051256 filed on Apr. 30, 2015, which claims priority to GB Patent Application No. 1407641.8 filed on Apr. 30, 2014, the disclosures of which are incorporated in their entirety by reference herein.

FIELD OF THE INVENTION

The present invention relates to flow methods, such as flow diffusion and flow electrophoretic methods, and flow apparatus for analysing component mixtures, such as mixtures of polypeptides.

BACKGROUND

Many systems of fundamental or technological importance exist as polydisperse mixtures of heterogeneous components. The elucidation of the characteristic properties of the individual components in such mixtures is a crucial problem in fields ranging from analytical chemistry to biophysics.

Identifying constituents of complex mixtures is becoming increasingly important in modern biophysics since most processes in living organisms depend on the interplay of a variety of different constituents. In particular, early detection of many diseases may well be facilitated by monitoring the protein levels in the human body.

In spite of this pressing need for methods to analyse complex solutions of biomolecules, few technologies provide the necessary accuracy and resolution. And those that do 2D gel electrophoresis or mass spectrometry, for instance are either time-consuming, expensive, or both. Furthermore, techniques such as gel electrophoresis does not provide quantitative information on the properties of the analytes.

The separation and detection of components within fluid flows, such as microfluidic flows, presents a number of challenges. Given the recent increased interest in fluidic techniques for the reaction, separation and detection of components, there is interest in developing methods and devices that allow components to be separated and analysed in a continuous flow system.

The present inventors have established a fluidic method for analysing a component, including a component in a multicomponent mixture.

SUMMARY OF THE INVENTION

The present invention provides a method of analysing a component using fluidic techniques. Generally, the invention provides a method comprising the step of distributing a component across a fluid flow, separating a part of the fluid flow containing the component, and then subsequently distributing the component across another fluid flow. The behaviour of the component in a distribution step is indicative of an inherent chemical or physical property of that component, and thus each distribution step may be used to obtain characterising information for that component. The provision of two distribution steps therefore allows the user to identify two properties of the component.

The behaviour of a first component in a distribution step may differ to the behaviour of a second component, leading to a different distribution of the two components across a fluid flow. A part of the fluid flow containing the first component is collected and in this way one component may be at least partially separated from another component.

In a first distribution step, the behaviour of the second component may be the same as the first component, for example for the reason that they share a common chemical or physical property. Separating a part of the fluid flow containing the first component will therefore also collect the second component.

A second distribution is undertaken, and in this second distribution the behaviour of the first and second components may differ, leading to a different distribution of the two components across a fluid flow. This step allows for the resolution of a multi-component mixture as the presence of two different components may be ascertained. A part of the fluid flow containing the first component is collected and in this way one component may be at least partially separated from another component. Thus, the techniques of the present invention may be used to separate components that share a common chemical or physical property, based on the differences in another chemical or physical property. The method of the invention makes use of a plurality of distribution steps. The use of plural distribution techniques allows for the identification and separation according to mutually independent physical and chemical properties for components within a multicomponent mixture. In this way the introduction of second and further distribution steps increases the resolution of the analysis method, as there is an extra dimension, which is capable of discriminating between components that were not otherwise separable in a first distribution step.

Accordingly, in a first aspect of the invention there is provided a method for analysing a component, the method comprising the steps of:
(iii) providing a distribution of the component across contacting first and second fluid flows, such as laminar fluid flows;
(iv) diverting a part of the first fluid flow, a part of the second fluid flow, or parts of the first fluid flow and the second fluid flow, wherein the diverted part is a third fluid flow which comprises the component;
(v) contacting the third fluid flow with a fourth fluid flow, such as to form a laminar flow; and
(vi) providing a distribution of the component across contacting third and fourth fluid flows, such as laminar fluid flows.

In one embodiment, the method further comprises the preliminary steps of:
(i) providing the component in a first fluid flow; and
(ii) contacting the fluid flow with a second fluid flow, such as to generate a laminar flow. In this embodiment, the method comprises the preliminary step of generating a distribution of the component.

In one embodiment, the method further comprises the subsequent step of:
(vii) diverting a part of the third fluid flow, a part of the fourth fluid flow, or parts of the third fluid flow and fourth fluid flow; wherein the diverted part is a fifth fluid flow which comprises the component. In this embodiment, a component may be at least partially separated, for example from another component present in the third fluid flow.

In one embodiment, step (vi) comprises the electrophoretic movement of the component into the fourth fluid flow. Here step (iii) may comprise the diffusion of the component into the second fluid flow. In one embodiment, step (vi) comprises the diffusion of the component into the fourth fluid flow. Here step (iii) may comprise the electrophoretic movement of the component into the second fluid flow. In one embodiment, step (vi) comprises the movement of the component is a response to an isoelectric point determination, also known as isoelectric focusing, ultracentrifugation, or magnetic separation.

In one embodiment, the method comprises the step analysing the component in a fluid flow. The fluid flow may be a third or fifth fluid flow. The fluid flow may be the contacting first and second fluid flows or the contacting third and fourth fluid flows.

In one aspect, there is provided a method for separating a first component from a mixture further comprising second and third components, the method comprising the steps of:
(i) providing a mixture of the first, second and third components in a first fluid flow;
(ii) contacting the fluid flow with a second fluid flow, such as to generate a laminar flow;
(iii) providing a distribution of the first, second and third components across contacting first and second fluid flows, such as laminar fluid flows;
(iv) diverting a part of the first fluid flow, a part of the second fluid flow, or parts of the first fluid flow and the second fluid flow, wherein the diverted part is a third fluid flow which comprises the first component and second components at least partially separated from the third component;
(v) contacting the third fluid flow with a fourth fluid flow, such as to form a laminar flow; and
(vi) providing a distribution of the first and second components across contacting third and fourth fluid flows, such as laminar fluid flows.

The method allows the first, second and third components to be at least partially separated from one another in two distribution steps, which are performed on a continuous fluid flow.

In one embodiment, the method further comprises the subsequent step of (vii) diverting a part of the third fluid flow, a part of the fourth fluid flow, or parts of the third fluid flow and the fourth fluid flow, wherein the diverted part is a fifth fluid flow which comprises the first component at least partially separated from the second component.

A further aspect provides a method for analysing a multicomponent mixture comprising a first and a second component, the method comprising the steps of:
(i) providing a mixture of the first and second components in a first fluid flow;
(ii) contacting the fluid flow with a second fluid flow, such as to generate a laminar flow; providing a distribution of the first and second components across contacting first and second fluid flows, such as laminar fluid flows;
(iv) diverting a part of the first fluid flow, a part of the second fluid flow, or parts of the first fluid flow and the second fluid flow, wherein the diverted part is a third fluid flow which comprises the first component at least partially separated from the third component;
(v) contacting the third fluid flow with a fourth fluid flow, such as to form a laminar flow;
(vi) providing a distribution of the first component across contacting third and fourth fluid flows, such as laminar fluid flows;
(vii) subsequently diverting a part of the first fluid flow, a part of the second fluid flow, or parts of the first fluid flow and the second fluid flow, wherein the diverted part is a third fluid flow which comprises the second component at least partially separated from the first component; contacting the third fluid flow with a fourth fluid flow, such as to form a laminar flow; and
(ix) providing a distribution of the second component across contacting third and fourth fluid flows, such as laminar fluid flows.

The method allows a first component to be separated in two sequential distribution steps, and following a change in the diversion step after the first distribution step, the second component may be separated in two sequential distribution steps. In this way, a plurality of physical and/or chemical characteristics of the first component may be determined, and a plurality of physical and/or chemical characteristics of the second component may be determined.

In one embodiment step (vii) includes altering the distribution of the first and second components across contacting first and second fluid flows, such as laminar fluid flows. In one embodiment, the first fluid flow is continuous through steps (iv) and (vii).

In a further aspect of the invention there is provided a flow apparatus for use in the methods of the invention. The flow apparatus comprises:
a first separation channel for first and second flows in contact, wherein the separation channel is adapted to permit lateral movement of components between contacting first and second flows;
a first flow separator, in fluid communication with and downstream of the first separation channel, the first flow separator being adapted to divert a part of the first fluid flow, a part of the second fluid flow, or parts of the first fluid flow and the second fluid flow, from the first separation channel, the diverted flow being a third flow; and
a second separation channel, in fluid communication with and downstream of the first flow separator, the second separation channel being for third and fourth flows in contact, wherein the separation channel is adapted to permit lateral movement of components between contacting third and fourth flows. These and other aspects and embodiments of the invention are described in further detail below.

DETAILED DESCRIPTION OF THE INVENTION

Figure 1:
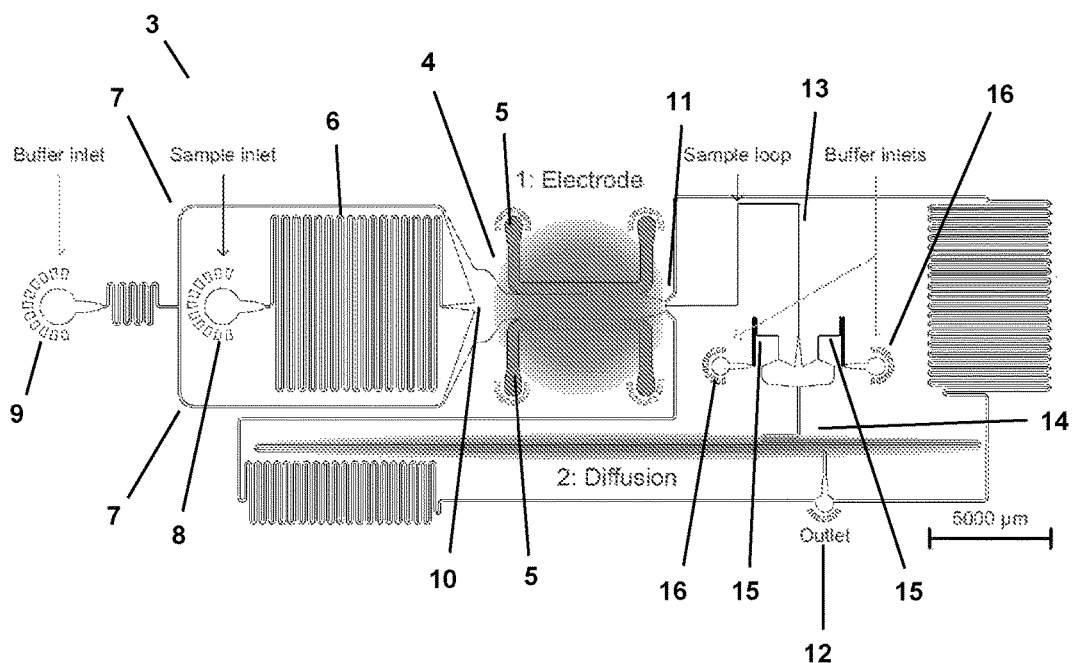
FIG. 1 is a schematic of a flow apparatus according to one embodiment of the invention for use in the analysis and/or separation of a component. The scale bar is 5,000.

The present invention provides methods and apparatus for analysing a component in a fluid, including a component in a multicomponent mixture.

The method of the present case provides an alternative approach for the analysis of complex mixtures by a modular fluidic strategy relying on laminar flow. Namely, a solution is preseparated under steady-state conditions according to physical properties before its contents are identified by means of another quantity through global analysis. In the present case the method is exemplified by the separation of analytes with respect to their size-over-charge ratios through microfluidic free-flow electrophoresis before subsequent separation by size via diffusion spectrometry.

As the methods of the invention typically occur under steady state, several separative modules can be added in series to multiplicatively increase the resolution of this technique, and different detection modules may be used.

The present inventors have previously described the use of fluidic techniques to analyse and separate a component in a fluid flow. This work is described in GB 1320146.2 (filed on 14 Nov. 2013), the contents of which are hereby incorporated by reference in their entirety. The present work now adapts this work to use separative distribution steps in series to allow for the separation and/or analysis of a component, for example a component in a multicomponent mixture. Using these techniques the inventors have established a two dimensional flow analysis and separation method, which is useful for studying low concentrations and small volumes of component-containing fluids, such as protein-containing fluids.

The methods of the invention may be conducted in a single device under constant fluid flow. A component is distributed across fluid flows in a first step. That component is then diverted, for example whilst simultaneously separating that component from other components, and the component is subsequently distributed across further fluid flows in a second step. Each distribution step allows the user to determine a property of the components, and each distribution step allows for the separation of that component from components having different properties. The use of a plurality of destitution steps may permit a component to be separated from other related components: the components may behave similarly in one distribution step, but may not do so in a second distribution step. In this way, a mixture of components may be analytically resolved, and the mixture may be at least partially separated, allowing for the at least partial purification of one component from another. The methods of the present case are performed in line, thus fluid containing a component distributed across the flow is separated, and a separated part of that flow containing the component is subjected to a downstream further distribution step.

The methods and apparatus of the invention are particularly well suited to miniaturisation, and in one embodiment there is provided the use of microfluidic techniques and microfluidic apparatus for the analysis and/or purification of a component. The provision of an apparatus having suitable microchannels, prepared using standard techniques, allows the methods of the invention to be performed using small volumes of fluids, as noted above.

The methods of the invention may also be used to analyse and/or separate a plurality of components in a multicomponent mixture. The diversion step, whereby one component is at least partially separated from other components may be used to collect other components. There are two main methods for achieving this.

First, the downstream end of a first separation channel may be provided with a plurality of flow separators. Each flow separator may be provided to divert a different part of the first and second flows. Thus, a plurality of flows may be collected. Where a plurality of flows is collected at the downstream end of a first separation channel, each of these flows may be permitted to flow into separate second separation channels where a further separation step may be performed. Optionally a second (or further) separation channel may be provided with a plurality of flow separators to allow the collection of components from different parts of the third and fourth flows. Each diverted flow may be analysed and/or collected as required. In this way a plurality of components may be separated in a continuous flow system.

Second, the conditions in a separation channel may be altered during the flow method to change the distribution profile of a component or a multicomponent mixture at the downstream end of the separation channel. The change in distribution profile results in the flow separator collecting a part of the first fluid flow and/or a part of the second fluid flow that has a different composition, for example a different component or a different quantity of components.

The conditions in the flow channel may be changed in a number of ways. For example the flow rate may be increased or decreased to alter the distribution profile at the downstream end. The conditions that are used to move the component from one flow to another may be altered in order to affect the distribution profile. Where electrophoretic conditions are employed, the applied field across the channel may be altered, thereby altering the degree of deflection of components across the flows. A change in the deflection of a component will result in an altered distribution profile at the downstream end. The change in the distribution profile may be achieved during the methods of analysis thereby allowing for the analysis of a plurality of components on a single flow.

A change in distribution profile as used herein may refer to a change in the shape of the profile (i.e. the change in the population of components at locations across the flows). This includes a change in the location of the maximum population of a component of components at a location across the channel.

The methods of the invention also allow a component to be quantified. The techniques described herein allow for the separation and collection of all components in a fluid flow. The methods are non-destructive and therefore all inputs into the system are collected at the output. The ability to at least partially separate one component from another allow the amount of one component to be quantified relatively, with respect to the overall population of components, or absolutely. The use of standard analysis techniques, such as fluorescence spectroscopy, provides a direct link between the intensity of a detected signal and the concentration, and therefore amount, of a component present.

General methods for the analysis and purification of a component are described in further detail below.

General Methods

The method of the first aspect of the invention generally looks to analyse, such as characterise or quantify, a component in a solution. Additionally or alternatively the method may be used to at least partially separate a component from other components in a multicomponent mixture.

The methods involve the distribution of a component across a series of fluid flows. The distributions of the component across those fluid flows is indicative of physical and/or chemical properties of that component, and the distribution will differ from other components, which do not share the physical and/or chemical properties of the component.

The distribution of a component across fluid flows may be in response to an applied stimulus, such as an applied field, or the distribution may make use of inherent characteristics of the component, such as the diffusive characteristics of the component, which is related to the component size. The distribution steps are carried out in a single flow device and with a continuous fluid flow.

A first fluid flow comprising one or more components is brought into contact with a second fluid flow in a first separation channel, such as to generate a laminar flow. The contacted flows are permitted to flow along the first separation channel and components in the first fluid flow are permitted to move into the second fluid flow, to provide a distribution of the components across the first and second fluid flows. The movement of the component into that second fluid flow may be diffusion or electrophoretic movement, for example.

A part of the first fluid flow, a part of the second fluid flow, or parts of the first and second fluid flows is subsequently diverted into a first diversion channel wherein the diverted part is a third fluid flow which comprises the component, optionally together with other components. The diversion step may result in the at least partial separation of the component from other components in the first and second fluid flows.

The third fluid flow comprising the component is brought into contact with a fourth fluid flow in a second separation channel, such as to generate a laminar flow. The contacted flows are permitted to flow along the second separation channel and components in the third fluid flow are permitted to move into the fourth fluid flow, to provide a distribution of the components across the third and fourth fluid flows. The movement of the component into that fourth fluid flow may be diffusion or electrophoretic movement, for example.

The conditions under which the component is permitted to move into the fourth fluid flow differ from those used to distribute the component into the second fluid flow. It is the use of a different distribution technique that provides additional analytical information to the user, and provides a further separation step for purification of the component from other components.

Optionally, a part of the third fluid flow, a part of the fourth fluid flow, or parts of the third and fourth fluid flows is subsequently diverted into a second diversion channel wherein the diverted part is a fifth fluid flow which comprises the component, optionally together with other components. The diversion step may result in the at least partial separation of the component from other components in the third and fourth fluid flows.

In one embodiment, a distribution of a component across contacting first and second fluid flows is provided by electrophoretic movement of the component into the second fluid flow, and a distribution of a component across contacting third and fourth fluid flows is provided by diffusion of the component into the fourth fluid flow. In an alternative embodiment, a distribution of a component across contacting first and second fluid flows is provided by diffusion of the component into the second fluid flow, and a distribution of a component across contacting third and fourth fluid flows is provided by electrophoretic movement of the component into the fourth fluid flow.

The separation channels and diversion channel, and analysis channels and reagent channel, where present, are parts of a fluidic device. The fluidic device, particularly the analysis channel, is adapted for use with a detector for the components.

The flow rate of each flow is maintained at a substantially constant level during the separation and diversion steps. The separation and diversion steps may be undertaken only when a stable flow is established in the channels of each section.

The component may be or comprise a polymer, such as a biopolymer. The component may be or comprise a polypeptide, a polynucleotide or a polysaccharide. Each of these may be regarded as a biopolymer. In one embodiment, the component is or comprises a polypeptide. In one embodiment, the component is or comprises a protein. The component may be part of a multicomponent mixture. The separation step may therefore be used to at least partially separate the component from other components. For example, the techniques described herein allow for separation based on size or charge-to-size ratio, amongst others. Where the component is a protein, the other components may be other proteins, or may be the same protein in a different state of aggregation to the component. The present invention is suitable for analysing a component, such as a polymer molecule, having a molecular weight of 300 Da or more, 500 Da or more, 1,000 Da (1 kDa) or more, or 2 kDa or more. The present invention is suitable for analysing a component having a molecular weight of 5 kDa or less, 10 kDa or less, 50 kDa less, 100 kDa, 200 KDa, 500 kDa or 1,000 kDa less.

The present invention is suitable for analysing a component having a hydrodynamic radius of at least 0.05 nm, at least 0.1 nm, at least 0.5 nm, at least 1 nm, or at least 5 nm. The present invention is suitable for analysing a component having a hydrodynamic radius of at most 10 nm, at most 15 nm, at most 25 nm, at most 50 nm, at most 100 nm, or at most 200 nm, or at most 500 nm.

In particular, the present invention is particularly suitable for analysing components having hydrodynamic radii in the range 0.5 to 500 nm, such as 0.5 to 200 nm, such as 0.5 to 15 nm.

A component may have an analytical label to allow for the detection of the component. The component may be labeled prior to its use in the methods of the invention. Alternatively a component may be labeled as part of the methods of the invention.

In one embodiment, the component is provided with one or more chromophore labels, such as fluorophore labels.

In some embodiments, it is not necessary to label a component, as the component may inherently possess functionality that is detectable using the spectroscopic methods described above, such as fluorescence spectroscopy. For example, where a component possesses fluorescently active groups these may be used for the fluorescent detection of that component.

Components that are or comprise polypeptides may possess the amino acids tryptophan, tyrosine and phenylalanine, the side chains of which have fluorescent activity. However, the presence of these residues may not be sufficient to allow the detection of the component. For example, the tyrosine and phenylalanine fluorescent activity is very weak, and is therefore hard to detect. Where there are few tryptophan, tyrosine and phenylalanine amino acid residues within the polypeptide, the fluorescent signal may be weak. In these cases it may be preferable to provide a fluorescent label having a greater fluorescent activity. The OPA-derived label is an example of a label that may be used.

In one embodiment, the multicomponent mixture comprises agglomerations of components, including proteins, such as monomer, dimer and trimer species, or other higher order agglomerations. Thus, the techniques described herein may be used to separate and analyse protein-protein interactions. Optionally, a component in a fluid flow may be analysed. An analysis may be performed of the component distributed across the first and second fluids, such as in the first separation channel. An analysis may be performed of a component within the third fluid, such as in the first flow separator. An analysis may be performed of the component distributed across the third and fourth fluids, such as in the second separation channel. Where a fifth fluid flow is diverted from the third and fourth fluid flows, an analysis may be performed of a component within the fifth fluid, such as in the second flow separator.

Fluid Flows

The present invention provides methods of separation and analysis for component provided in a fluid flow. In one embodiment, a reference to a fluid flow is a reference to a liquid flow.

A fluid flow may be an aqueous flow. An aqueous flow may include other solvents, such as DMSO, alkyl alcohol and the like.

The devices of the invention may be adapted for use with fluid flows, and may be adapted for use with aqueous fluid flows.

In embodiments of the invention, the component is initially provided in a first fluid flow. The component is preferably dissolved in the first fluid.

In one embodiment, the first fluid allows a component or components to remain in its native state. Where the component is a biomolecule, such as a protein, the fluid flow may be a suitable buffer. Thus, the salt content and pH, amongst others, may be selected to retain the component in its native state.

The second fluid flow may be identical to the first fluid flow, except that the second fluid flow does not contain the component. Similarly, the fourth fluid flow may be identical to the first fluid flow, except that the second fluid flow does not contain the component.

The third fluid flow is a diverted part of the first and/or second fluid flows. The fifth fluid flow, if such a flow is collected, is a diverted part of the third and/or fourth fluid flows.

The first and second fluid flows are brought into contact, and component in the first flow is permitted to move into the second flow to generate a distribution of the component across first and second fluid flows. The contacting flows may be a laminar flow of the first flow with the second flow.

The third and fourth fluid flows are brought into contact, and component in the third flow is permitted to move into the fourth flow to generate a distribution of the component across first and second fluid flows. The contacting flows may be a laminar flow of the third flow with the fourth flow.

In certain embodiments of the invention the diverted third fluid flow may be mixed with a labeling flow prior to contacting the fourth fluid flow, thereby to label the component in the diverted fluid flow for analysis. Optionally the diverted third fluid flow may be mixed with a denaturing flow, for example flow prior to third fluid flow contacting a labeling flow and the fourth fluid flow. The denaturing flow may be provided to denature a component, for example to make that component suitable for labeling.

These labeling and optional denaturing steps are less preferred, and the diverted third fluid flow is typically contacted with the fourth fluid flow directly after it is diverted from the first and/or second fluid flows. Thus, the component that is diverted is generally not modified prior to its distribution across the third and fourth fluid flows.

A fifth fluid flow, if such a flow is collected, may be mixed with a labeling flow thereby to label the component in the diverted fluid flow for analysis. Optionally the diverted fifth fluid flow may be mixed with a denaturing flow, for example flow prior to fifth fluid flow contacting a labeling flow. The denaturing flow may be provided to denature a component, for example to make that component suitable for labeling.

Where the methods of the invention contain multiple lateral distribution steps, such as two, three of four distribution steps, any labeling and denaturing steps may be performed only after the last of those distribution steps. In other embodiments a component is labeled prior to its use in the methods of the invention.

The labeling flow is typically a liquid flow, such as an aqueous flow, containing reagents suitable for labeling a component. Suitable labeling techniques for use in flow methodologies are known in the art, and are described herein.

The denaturing flow is typically a liquid flow, such as an aqueous flow, containing reagents suitable for denaturing a component.

Further details on labeling and denaturing are provided below.

Distribution and Separation

The method of the invention includes the step of providing a distribution of a component across the first and second fluid flows, and then subsequently providing a distribution of a component across third and fourth fluid flows. The distribution is typically a non-uniform distribution of the component across the first and second fluid flows, and a non-uniform distribution of the component across the third and fourth fluid flows.

A distribution step is the step in the method of the invention where the component is permitted to move from one fluid flow to another fluid flow. In the present case, the term distribution refers to the lateral distribution of a component across the fluid flows. This may be regarded as a distribution that is orthogonal to the flow direction.

As described herein, the distribution may comprise the diffusion of the component into the second or fourth fluid flows or electrophoretic movement of the component into the second or fourth fluid flows. Other distribution techniques may be used.

The distribution is the lateral distribution of the component or a multicomponent mixture comprising the component.

A lateral distribution may be contrasted with a distribution of components along the fluid flow. For example, it is known in the art that fluidic methods may be used to separate components in a fluid flow based on the Taylor dispersion of a species in a fluid channel. For example, US 2011/264380 describes methods for determining the hydrodynamic radius of a polydisperse species. The species to be analysed is mixed with a monodisperse standard. The resulting mixture is added to a carrier fluid flowing along a capillary tube and the Taylor profile of the mixture as it exits the capillary is recorded. The work of US 2011/264380 does not include the step of performing a second distribution step after performing a first distribution of the component along the fluid flow.

The Ramsey group have described electrophoretic methods for separating proteins, however, the proteins are separated along the fluid flow and there is no non uniform distribution of the components across the flow (see e.g. Liu et al. *Anal. Chem.* 2000, 72, 4608; Jacobson et al. *Anal. Chem.* 1994, 66, 4127; Jacobson et al. *Anal. Chem.* 1994, 66, 3472). This may be regarded as a temporal rather than a spatial distribution. As noted previously, in contrast, the present invention allows components to be spatially separated under steady-state, permitting long exposure times for the efficient detection of low concentration samples.

Herling et al. and Kamholz et al. have described methods for the lateral distribution of components across fluid flows using electrophoretic and diffusion sizing techniques respectively. However, these documents do not describe the use of a plurality of lateral distribution techniques in series and they do not describe the diversion of a part of a fluid flow.

The separation approaches described herein are largely insensitive to the nature of the solvent conditions used in the flows. Thus, it is possible to study biological molecules, such as proteins, under their native conditions. In this way the behaviour of a component in the separation step is a characteristic of that component in its native state. There is no need for the analysis to include a calibration step to convert the behaviour of a component under foreign conditions to an expected behaviour under natural conditions.

Where the component is a part of a mixture (a multicomponent mixture), the component and other components of the mixture may be disturbed across the channel, thereby to provide a distribution profile for all components across the first and second fluid flows, and across the third and fourth fluid flows.

The first diverting step may be performed before the component has reached the boundary of the second fluid flow (i.e. the channel wall). Where the component is part of a multicomponent mixture, the diverting step may be performed before any component in the multicomponent mixture has reached the boundary of the second fluid flow.

Similarly, where a second diverting step is performed, this may occur before the component has reached the boundary of the fourth fluid flow (i.e. the channel wall). Where the component is part of a multicomponent mixture, the diverting step may be performed before any component in the multicomponent mixture has reached the boundary of the fourth fluid flow.

The distribution of a component across contact fluids may be altered by appropriate changes to the distribution technique.

The distribution profile is dependent upon the technique for distributing the component, and the time permitted for the distribution. Typically, the time permitted for distribution is such that components in the first or third fluid flow have not reached the boundary of the second or fourth fluid flow. For example, the flow residency time of the first and second flows in the separation channel may be selected such that components in the first fluid flow do not have time to reach the boundary under the separation conditions employed.

In one embodiment, the distribution of the component may be diffusion from the one flow to another flow, such as first to second or third to fourth flows. The rate of diffusive transport is proportional to the diffusion coefficient D of the component and inversely proportional to the hydrodynamic radius rho Thus, smaller components are expected to diffuse into a contacting fluid flow at a greater rate than larger components. For example, in a diversion step, the diversion of a part of the second fluid flow close to the boundary of the second fluid flow at the wall will collect those components having a smaller size. The diversion of a part of the second fluid flow close to the laminar boundary with the first fluid flow will allow collection of those components having a larger size. It follows that the diversion of a part of the second fluid flow that is between the laminar boundary and the channel boundary will allow collection of those components of intermediate size.

The size of the components diverted will depend upon the location of the flow separator in across the separation channel. The range of components that are diverted will depend upon the relative size of the diverted part compared to the total width of the first or second fluid flow, and the part of the flow that is diverted.

A diversion step may collect a part of the first or third fluid flows. Using a diffusion separation technique, the smaller components in the first or third fluid flows are expected to deplete more rapidly than the larger components as the smaller components diffuse into the second or fourth fluid flows at a greater rate.

In one embodiment, the distribution of the component may be electrophoretic movement from the first flow to the second flow or the third flow to the fourth flow. The rate of electrophoretic transport is proportional to the charge-to-size ratio of the component. Thus, components having a large charge and/or a small size are expected to have a greater electrophoretic movement compare to those components having a smaller charge and/or size.

Where electrophoresis is used to separate components, the second or fourth fluid flows are typically provided at both sides of the first fluid and third fluid flows respectively. During electrophoresis negatively charged species may be deflected into one of the second or fourth fluid flows, whilst positively charged species are deflected into the other of the second or fourth fluid flows.

Thus, components having a high charge-to-size ratio are expected to move (divert) into the second or fourth fluid flows at a greater rate than components having a low charge-to-size ratio. Accordingly, in the diversion step, the diversion of a part of the second or fourth fluid flow close to the boundary of the second or fourth fluid flow at the wall will collect those components having a high charge-to-size ratio.

The diversion of a part of the second or fourth fluid flow close to the laminar boundary with the first or third fluid flow will allow collection of those components having a low charge-to-size ratio. It follows that the diversion of a part of the second or fourth fluid flow that is between the laminar boundary and the channel boundary will allow collection of those components of intermediate charge-to-size ratio The charge-to-size ratio of the components diverted will depend upon the location of the flow separator in across the separation channel. The range of components that are diverted will depend upon the relative size of the diverted part compared to the total width of the first or second fluid flow, and the part of the flow that is diverted. It will be appreciated that the diversion of a part of the second fluid flow may collect only those species that have a negative or positive charge.

Where an electrophoretic method is used, the voltage applied across the channel may be selected appropriately for the degree of deflection required. In one embodiment, the applied voltage is at most 5 V, at most 10 V or at most 15 V. In one embodiment, the applied voltage is at least 0.1 V, at least 0.5 V, or at least 1.0 V. The voltage may be varied during the method in order to change the degree of deflection and thereby alter the component that is collected in the diversion step. Described above are diffusive and electrophoretic methods for distributing a component across first and second fluid flows. Alternative methods for the distribution of a component may be used. Examples include isoelectric point determination, also known as isoelectric focusing, ultracentrifugation, and magnetic separation, for example of metalloproteins.

Electrophoretic methods including but not limited to dielectrophoresis, isoelectric point determination, also known as isoelectric focusing and isotachophoresis, are used to separate components across first and second fluid flows. Dielectrophoresis is a common electrophoretic method used for the separation of components with a neutral charge across first and second fluid flows, by exerting a force on the dielectric particles within a non-uniform electric field. Separation of components by dielectophoresis is dependent on, but not limited, to the dielectric properties and size of the component, in addition to the strength of the applied field.

Another example of an electrophoretic method used to separate components is isoelectric point determination, also known as isoelectric focusing. Components are separated across the first and second fluid flows according to their isoelectric point. An electrical field is applied and the component migrates through the pH gradient. Individual components are immobilized in the pH gradient as they approach their specific isoelectric point.

Isotachophoresis method is used to selectively separate analytes based on their ionic mobility upon the application of a fixed electrical current.

In addition, thermophoresis technique is used to observe movements of different components through a temperature gradient across first and second fluid flows. A temperature gradient can be induced but not limited to by an infra-red laser. The diffusion rate of components through a temperature gradient is dependent on, but not limited, to its size, charge, conformation and hydration shell.

The method of the invention comprises the step of diverting a part of the first or second flows, or diverting parts of the first and second fluid flows. The analysis of a part of a fluid flow allows the user to determine the quantity and identity of material in a portion of the diffusion profile.

In an alternative aspect the diverting step includes the step of diverting all of the first fluid flow or all of the second fluid flow.

The separation step may be distinguished over chromatographic and Taylor separation methods, and the alternative electrophoretic techniques (capillary electrophoresis) of the Ramsey group, where components are separated along the fluid flow. Such techniques may be regarded as separating components in time. In contrast, the separation methods employed in the present case separate components in space.

In one embodiment, the first fluid flow is provided as a central flow between two laminar second fluid flows. Thus, a component in the first fluid flow may be distributed into one or both of the second fluid flows.

In one embodiment, the distribution of a component or components across the flows is measured. The distribution of a component or components may be measured at a plurality of locations along the fluid flow. The measurements are made before the laminar flow is diverted. Where diffusion distribution techniques are used, for example, each location represents a particular diffusion time. Such measurements may be made only when the component has an inherent functionality that allows it to be detected, or the component has been provided with such e.g. in the form of a label prior to its use in the method of the invention. Where a component lacks such functionality, it may be provided with functionality in a later labeling step.

In the present invention the step described above is not necessary as information relating to the distribution of the component may be recorded from the diverted flow, as described herein.

Diversion

The method of the present invention includes the step of diverting a part of the first and second fluid flows. The diverted part of the fluid flow contains a component, which is separated from the remaining portion of the first and second fluid flows. The diverted part is a third fluid flow.

The diversion step takes a part of the first fluid flow, or a part of the second fluid flow, or parts of the first and second fluid flows. This diversion step may be referred to as the first diversion. In one embodiment, the diversion step takes a part of the second fluid flow.

Where reference is made to the diversion of parts of the first and second fluid flows, this is a reference to the diversion of a part of the first fluid flow and a part of the second fluid flow. The diversion of this part of the laminar flow includes the boundary where the first fluid flow and the second fluid flow contact.

In an alternative aspect the diversion step takes all of the first fluid flow or all of the second fluid flow. Generally, this is not preferred as the diversion of all of one fluid flow will not allow for the adequate separation of components. The step may be used where, for example, there is a clear distribution of one component into the second fluid flow, and the retention of another component in the first fluid flow. Here, the diversion of one of the first and second fluid flows has the effect of substantially removing one component from another. However, where there is distribution of both components across the first and second fluid flows, it is preferred that a part of the first and/or second fluid flows is diverted.

The diversion step separates a part of the fluid flow for subsequent further distribution between third and fourth fluid flows. The part of the fluid flow taken represents a portion of the lateral distribution profile established in the separation step. The diversion step is the separation of a fraction of the total width of the fluid flow, or a fraction of the width of the first or second fluid flow. The fraction of the fluid flow that is diverted is not particularly limited and is selected based on the component for analysis, and, where present, other components in a multicomponent mixture.

The diverting step refers to the separation of a portion of the flows that corresponds to a part of the first fluid flow and/or second fluid flow. When the first and second fluid flows first contact there is a clear distinction between first and second fluid flows. The former carries the components, and the latter carries no components. At the downstream end of the separation channel components from the first fluid flow move across into the second fluid flow to generate a distribution of components across the first and second fluid flows. Here, there is no clear boundary between a first fluid and a second fluid.

In the present case, a reference to the diversion of a fluid flow is a reference to a particular cross section portion of the contacting first and second fluid flows, such as a particular region in the channel. That region of the channel is said to be a part of the first fluid flow if it corresponds to a region in the channel at the upstream part of the channel, such as the junction, where the first fluid flow first contacts the second fluid flow.

For example, when the first and second flows first contact, a contacting flow may be established at the upstream part of the channel where the first fluid flow occupies half of the channel width and the second fluid flow occupies the remaining half of the channel width. A diverted part of the fluid flow may be referred to as a diverted part of the first fluid flow if that part is taken from the half of the channel width that was originally occupied by the first fluid flow. In this situation the demarcation between first and second fluid flows is simply the centre line in the channel.

The location of the first and second fluids at the downstream end of the contacting flows may be determined from the distribution of components held with a first fluid flow. For example, in a diffusive distribution, a very large component will have negligible diffusion into the second fluid flow. At the downstream end the very large component will be retained in the first fluid flow. In an electrophoretic separation an uncharged component will have a negligible deflection in response to the applied filed, and therefore will not substantially move out of the first fluid flow.

Optionally, the method of the present invention includes the step of diverting a part of the third and fourth fluid flows. The diverted part of the fluid flow contains component, which is separated from the remaining portion of the third and fourth fluid flows. The diverted part is a fifth fluid flow. This diversion may be referred to as the second diversion step.

The diversion step takes a part of the third fluid flow, or a part of the fourth fluid flow, or parts of the third and fourth fluid flows. In on embodiment, the diversion step takes a part of the fourth fluid flow. The references below to the diversion of certain amounts of the first and second flows may be applied to the diversion of certain amounts of the third and fourth flows respectively.

In one embodiment, the diversion step diverts at least 5%, at least 10%, at least 15%, at least 20%, at least 25%, at least 30% of the first fluid flow, the second fluid flow or the first and second fluid flows. In one embodiment, the diversion step diverts at most 40%, at most 50%, at most 60%, at most 75%, at most 85% of the first fluid flow, the second fluid flow or the first and second fluid flows. In one embodiment, the diversion step diverts an amount of the first fluid flow, the second fluid flow or the first and second fluid flows from a range where the lower and upper values for the range are selected from the minimum and maximum values given above.

In one embodiment, the diversion step diverts a part of the second fluid flow. In one embodiment, the part second fluid flow that is diverted may be the part that extends from the boundary of the second fluid flow with the first fluid flow across at most 5%, 10%, 15%, 25%,50% or 75% of the width of the second fluid flow. In one embodiment, the part of the second fluid flow that is diverted may be the part that extends from the boundary of the second fluid flow with the channel wall, across at most 5%, 10%, 15%, 25%, 50% or 75% of the width of the second fluid flow. In one embodiment, the part second fluid flow that is diverted does not include the part that extends from the boundary of the second fluid flow with the first fluid flow or the part that extends from the boundary of the second fluid flow with the channel wall. Thus, the diverted part is an intermediate part of the second fluid flow. This intermediate part may be at most 5%, 10%, 15%, 25%, 50% or 75% of the width of the second fluid flow. The part of the fluid flow that is directed may depend upon the identity of the component to be detected.

As noted in the Distribution and Separation section above, the diffusion and electrophoretic separation techniques may be used to obtain a distribution of a component or components across the first and second fluid flows and second and third fluid flows. The part of the fluid flow that is diverted may be chosen in order to analyse components having a property of interest, e.g. a particular size or a particular charge-to-size ratio.

The methods of the invention may be used to divert components that differ in the property of interest. The part of the first or second fluid flow that is collected may be changed in order to divert alternative components. The separation techniques may also be adapted to alter the distribution of components at point where the flows are deviated. For example, the diffusion time in a diffusion separation may be altered with changes in flow rate, or changes in the length of the separation channel (as described in PCT/GB2013/052757). The deflection of components in an electrophoretic separation may be altered with changes in flow rate or changes in the applied field (for example as described by Herling et al.). It is not necessary to separate the combined flows as a fraction of the flow height (or depth). In the device of the invention, the fluid flows may be separated by appropriate placement of exit channels at the downstream end of the separation channel. A diversion channel may be located at an appropriate lateral location, to divert fluid from the required part of the first or second fluid flow (or flows) from the separation channel.

The remaining parts of the laminar flow that are not diverted may be collected, or those parts may be analysed, as described in further detail below.

In one embodiment of the invention a plurality of fluid flow parts is diverted. At least one diverted part of the laminar fluid flow is analysed. Where a diverted part of the laminar flow includes a part of the second fluid flow, that diverted part is analysed.

Each diverted flow is a part of the first fluid flow, a part of the second fluid flow, or parts of the first fluid flow and the second fluid flow. One of the diverted parts comprises a component. Where the first fluid flow comprises a plurality of components, each of the plurality of fluid flow parts may contain a component.

The diverted flow is subsequently analysed downstream as described below.

In one embodiment of the invention, a diverted part of the first and second flows is recombined with other parts of the flow after analysis. Thus, all components in the original first and second fluid flows may be collected for further analysis and use.

Labelling

The methods of the invention may include a labeling step where a component is labeled within the flow apparatus, for example for ease of detection and/or isolation.

The inventors have established methods for labeling components, such as proteins, in flow within a separation device. Suitable labeling techniques are described in the inventors earlier application GB 1320146.2 filed on 14 Nov. 2013, the contents of which are hereby incorporated by reference in their entirety.

In one embodiment, component that is present in a diverted flow is labeled for analysis. A component may be labeled in the third fluid flow before a second separation, or a component may be labeled in the third fluid flow after a second separation.

In one embodiment, a component is labeled prior to its use in the methods of the invention. Thus, a further labeling step is not required. In one embodiment, a component is labeled after it has been collected at the end of a method. Here, it is not necessary to label the component during the method. In one embodiment, a component is labeled prior to analysis. A component may be labeled in a diverted flow.

In one embodiment, a diverted flow is contacted with a reagent flow, and one or more reagents within the reagent flow are permitted to mix, optionally to react, with a component in the diverted flow. After appropriate mixing and reaction, an analysis is performed. The component may be analysed within the fluid flow. The reagent may be a label or may generate a detectable label upon reaction.

In one embodiment, of the invention the component is labeled after separation, for example after diversion. The labeling process is a part of the detection step for the analysis of the component.

In one embodiment, the label is a latent label. A latent label is a label that is spectroscopically active, such as fluorescently active, only when it is associated with the component. Otherwise, the label is spectroscopically inactive. Thus a latent label is detectable only when it is associated with the component, and label that has not formed an association with the component remains spectroscopically inactive. It follows that the detection of the component is simplified, as it is not necessary to remove unreacted label from the fluid flow, or to discount the contribution of the label to the recorded spectroscopic signal. For example, and as described herein, a reaction with a component may remove a group present on the label that quenches its fluorescence, the reaction thereby removing the quench. In another example, the label, such as a fluorophore group, is formed during the labeling reaction, for example through the formation of an extended conjugated system.

In one embodiment, the label is covalently bonded to the component. Thus, the labeling step includes the formation of one or more covalent bonds between the label and the component. The covalent bond may be formed with an amino, hydroxy or thiol group on the component. Where the component is a polypeptide, such as a protein, the covalent bond may be formed with the amino acid residue side chain functionality.

In other embodiment, non-covalent labels may be used, which may be specific or nonspecific to the component. Examples of non-covalent labels for components are described by the Ramsey group (see, for example, Liu et al. *Anal. Chem.* 2000, 72, 4068).

In one embodiment, the label reacts with amino functionality of the component, such as primary amino functionality ($-NH_2$). Where the component is or comprises a polypeptide, such as a protein, the label may react with lysine residues of the polypeptide.

In one embodiment, the label is derived from ortho-phthalaldehyde or an orthophthalaldehyde-containing compound.

The present inventors have found that ortho-phthalaldehyde (OPA) may be used as a latent covalent label. OPA may be reacted with one or more amino groups of the component to form a detectable fluorescent label. OPA is preferably reacted with a component amino group in the presence of a thiol containing reagent, such as an alkyl thiol, such as ethanol (BME).

In one embodiment, the labeling reaction is a substantially quantitative reaction. Thus, in one embodiment, substantially all the diverted component is labeled. Further, where a component contains a plurality of groups that are capable of reacting with the label, substantially all of those groups react with the label. Thus, the recorded spectroscopic signal may be used to directly quantify the component in the flow. Moreover, a high degree of labeling (i.e. all components labeled and/or components having multiple labels) generally improves the detection of the component in the fluid flow. This is particularly important under flow conditions where the component in present at very low concentrations.

The labeling reaction should be suitable for use in a flow system. Thus, it is important that the labeling reaction occur in a relatively short time frame, as the residency time of the fluid in the device is not large. The present inventors have found that the OPA label reacts rapidly with component such as proteins, and is therefore suitable for use in the flow methods described herein. In one embodiment, the labeling reaction time is at most 5 s, at most 2 s, at most 1.5 s or at most 1 s. The labeling reaction time may refer to the time taken to label at least 50 mole %, at least 80 mole % or at least 90 mole % of components, preferably 90 mole %. In one embodiment, the labeling reaction time may refer to the reaction half-time.

Where the method of the invention includes the step of labeling the diverted component, the diverted flow is contacted with a fluid flow comprising the label (the label fluid flow) optionally together with associated reagents for the labeling reaction. The diverted flow and the label fluid flow are brought together at a junction downstream of the flow separator.

The component and label are permitted to intermix within the fluid flows thereby to label the component. The label flow and diverted flow may be permitted to flow along a mixing channel to ensure adequate time for labeling within the device, for example to allow for adequate time for labeling prior to spectroscopic analysis.

In one general embodiment, the secondary, tertiary and/or quaternary structure of the component, such as the secondary or tertiary structure, preferably tertiary structure, is altered after the separation step, prior to analysis. Using the labeling methods described herein, the present inventors have found that is it not necessary to disrupt the secondary structure of a component, and it is sufficient to alter the tertiary and/or quaternary structure, where present, in order to allow appropriate labeling.

In one embodiment, the component is denatured prior to analysis. The denaturing step is intended to make available functional groups on and within the component that may assist in the labeling and/or detection of the component. For example, where the component is a polypeptide, such as a protein, the denaturing step may expose amino, hydroxy and thiol functionality for reaction with a label.

The denaturing of the component may be effected by the addition of a denaturing reagent into the fluid flow. For example, where the component is a polypeptide SDS may be used as a denaturing reagent. The denaturing step is not limited to the use of denaturing reagents and environmental changes, such as temperatures, may be used to achieve a denaturation.

The component may be denatured prior to labeling. Separation of the denaturing and labeling steps may be undertaken in order to minimise the precipitation of the component, which may occur during a combined denaturing and labeling step.

Where the denaturing step makes use of a denaturing reagent, the denaturing reagent may be provided in a fluid flow (denaturing flow) that is contacted with the diverted flow. The diverted flow and the denaturing fluid flow are brought together at a junction downstream of the flow separator. The component and denaturing reagent are permitted to intermix within the fluid flows thereby to denature the component. The denaturing flow and diverted flow may be permitted to flow along a mixing channel to ensure adequate time for denaturing within the device, for example to allow for adequate time for denaturing prior to contact with a labeling flow (where used) or prior to spectroscopic analysis.

Where the method also includes the step of labeling the component, the labeling step is undertaken downstream of the denaturing step.

Alternatively, the component may be denatured and labeled in one combined step. A combined denatured and labeled step may be used where there is little risk of precipitation of the components. Thus, in one embodiment, the label fluid flow additionally comprises the denaturing reagent. As shown herein, the junction where the diverted flow and the labeling flow (containing denaturant) are permitted to contact may be adapted to deal with denaturing problems. Thus, the surfaces of the fluid channels at the junction may be such that repel components in the fluid, for example hydrophilic surfaces may be used to prevent hydrophobic components adhering to the channel surfaces. Where the diverted flow is contacted with a label flow or a denaturing flow, it is preferred that the contents of a flow are permitted to rapidly mix with the contents of the flow with which it is contacted. The rapid mixing is to ensure rapid labeling or denaturing of the component. This should be contrasted with the step of contacting the first fluid flow and the second fluid flow, where it is not necessary or desirable to rapidly distribute the component across both the first and second flows. For example, in a diffusion separation step, the early establishment of a uniform distribution of components in the separation channel is undesirable, as this will not allow components to be separated. For the diffusion separation it is necessary to establish a non-uniform distribution profile across the first and second fluid flows.

Analysis and Detection

The method of the invention may comprise the step of analysing, such as detecting, a component in a fluid flow. The fluid flow may be a third or fifth fluid flow. The fluid flow may be the contacting first and second fluid flows or the contacting third and fourth fluid flows.

A component may possess functionality that allows it to be analysed within a fluid flow. Alternatively, as described herein, a component may be labeled to allow for detection of the component within a fluid flow. As described herein, fluorescence methods may be used for the detection of components, which may be suitably labeled with a fluorescent label.

An analysis step may include the preliminary step of preparing the diverted part of the fluid flow, including preparing the component, for analysis. Thus component in the third fluid flow or fifth fluid flows, where present, may be prepared for analysis as required. Where a component is prepared for analysis it is preferred that the component is labeled prior to its separation of after its separation. Typically, the component is analysed by a spectroscopy including UV/vis and fluorescent spectroscopy, and preferably by fluorescent spectroscopy. Fluorescent spectroscopy is particularly attractive as it affords high signal to noise ratios.

A component may be analysed whilst it is distributed across contacting flows, such as contacting first and second flows or contacting third and fourth flows. The recorded distribution profile may provide sufficient analytical information to resolve components within the distribution. It may not be necessary to divert a part of the flow in order to ascertain the composition of the contacting flows. Thus, certain methods of the invention include the step of determining the distribution of a component or components across a fluidic channel. There are no particular restrictions on the way that the movement of a component into a flow is measured, and the detection method employed may be based on the nature of the component to be detected.

The detector is one that is suitable for use with fluidic flow channels, and particularly microfluidic channels. Diffusion detection methods are well known in the art and are described by Kamholz et al., for example. Examples include UV-vis, fluorescent or luminescent spectroscopic methods, amongst others, as noted above.

The distribution of the component or components may be determined at a location in a distribution channel. However, particularly where two or more components are present, the distribution of components may be determined at two or more, such as three, four or five, locations along a channel. The method may include the step of determining the distribution profile of components at a plurality of locations in a channel.

At least one distribution measurement should be recorded before a component in the component flow has moved to the channel edge that is the boundary of the device to the blank fluid flow. For a sample of unknown composition a trial flow may be established to determine at what point the first component reaches the boundary edge. The first distribution measurement may therefore be taken upstream of this point.

Where multiple distribution measurements are made along a channel, the location of each the second and subsequent along the channel is not particularly limited. Typically, the subsequent measurements are taken at sufficiently further distances along the channel to give distribution profiles of useful difference to previous measurements.

In the methods of the present invention a laminar flow of the component flow and the blank flow is established and is provided in the small cross section channel. When the flow is established, a gradient of diffusion is provided along the small cross section channel. Data for different diffusion times may therefore be obtained simultaneously by analysing the diffusion profile at two or more locations along the small cross section channel.

The methods of the present invention do not require the separation of the blank flow from the component flow. Thus, the diffusion profile of the one or more components may be measured whilst the component flow and the bank flow are in contact.

Kamholz et al. describe the measurement of the diffusion profile at a single measurement location in a channel having a component flow (with a single component) and a blank flow.

In the fluidic system of US 2006/263903, a blank flow is diverted from the component flow after a period of contact in a cross channel region. At the contact point, a component in the component flow may diffuse into the blank flow. The separate blank flow is analysed and the amount of component quantified. To obtain a diffusion coefficient value for the component, it is necessary to take several measurements over time at a variety of different flow rates for the blank flow, the component flow, or both.

Prior to analysis, the components of interest may be labeled to allow their detection in the method of the invention. The label may take the form of a chemical group that is detectable by standard UV-vis, fluorescent or luminescent spectroscopy, for example.

Determination of Diffusion Coefficient

The present invention provides methods for determining the diffusion coefficient of a component or components in a fluid, for example in the first or second distribution steps.

Where a component fluid contains a monodisperse component, it is possible to determine the hydrodynamic radius of the component using standard techniques. Such are described, for example, by the Yager group (see Hatch et al. and Kamholz et al.).

Where the component fluid contains a polydisperse mixture of components, the present invention provides a method for determining the diffusion coefficients of two or more, or each component in the mixture. This is in contrast to methods known in the art which typically provide only an average diffusion value for the global mixture. In the method of the third aspect of the invention a plurality of diffusion measurements are recorded over different diffusion times.

As noted herein, the methods of the invention provide two laminar fluid flows. The methods are conducted at low Reynolds numbers where convection and diffusion are the only relevant mechanisms of mass transport. This simplifies the simulation of component movement within a channel.

Generally, the recorded diffusion spectra are deconvoluted with respect to a series of theoretical diffusion profiles determined for a range of components having hydrodynamic radii (and therefore diffusion coefficients) across the likely range of radii for the components under investigation. The deconvolution step fits the recorded data to the global profile made up from the most likely collection of individual theoretical diffusion profiles. The fit is made for the simplest solution consistent with experimental error. In context, the reference to the simplest solution is a reference to a minimal entropy regularisation.

The deconvolution of recorded diffusion profiles is made in reference to a generated basis function. The basis function is a collection of theoretical diffusion profiles where each theoretical profile is for a component having a particular hydrodynamic radius. The collection is made up of profiles for a range of hydrodynamic radii. For samples containing polypeptides, for example, the profiles span the range of likely radii for polypeptide components, such as 0.5 to 200 nm, such as 0.5 to 15 nm.

A regression analysis of the recorded data, using a least-squares fit, is undertaken with maximum entropy regularisation. In combination with the simulated basis function, the recorded spatial profiles may be deconvoluted into a spectrum of individual diffusion profiles.

The deconvolution methods described above are advantageous for they provide the solution within error of the best fit containing the least information. This in turn prevents so-called over-fitting of the data.

In further detail, the present methods allow accurate numerical calculations to determine kernels for species of given sizes. The diffusion profiles acquired in the flow experiment are then fitted globally to a linear superposition of the predicted kernels, where the amplitudes of each kernel are determined through a constrained least squares fitting where the coefficients are restricted to the interval 0 to 1 to ensure their physical interpretation as fractional concentrations. The residuals in the fit provide an estimate of the error in the measurement. A second series of least-squares fits is then performed, this time with minimum entropy regularisation. The entropic term is gradually increased in magnitude until the residuals of the regularised fi are different to those of the unregularised fit by the random error level. The coefficients for this final fit are then the simplest (minimal entropy) solution consistent with the experimental error.

The hydrodynamic radius of a component may be determined from the diffusion coefficient, as known in the art.

The diffusion profiles may also be used to determine the concentration of components in the component fluid, as known in the art.

Flow Apparatus

The present invention also provides a flow apparatus for use in the methods of the invention. The flow apparatus has suitable flow channels to allow a component to be distributed across fluid flows, and to allow parts of the fluid flows to be diverted.

Typically the flow apparatus has two separation channels in fluid communication. Each separation channel is adapted to allow two fluid flows to flow within, for example as laminar flows in the separation channel.

As described herein, the flow apparatus of the invention comprises first and second separation channels for first and second flows and third and fourth fluid flows. The first separation channel, and optionally the second separation channel, is in fluid communication with a downstream flow separator. Each separation channel is adapted to permit lateral movement of components between contacting flows, such as first and second flows, and third and fourth flows, and the flow separator is adapted to divert a part of the contacting flows. For example the flow separator is adapted to divert a part of the first fluid flow, a part of the second fluid flow, or parts of the first fluid flow and the second fluid flow, from the first separation channel.

The flow device of the present invention may be an integrated device, such as a monolithic device, having an integrated network of channels. Thus, the device has no dead volume and band broadening is limited.

The flow apparatus makes use of small fluidic channels, particularly microfluidic channels, and therefore very small sample volumes may be analysed. Thus, components provided in fluids of less than a microliter volume may be analysed by the methods described herein. Furthermore, fluid flow techniques can also be used to analyse very dilute samples, by appropriate increases in the measurement times.

The cross sections of the separation channels are typically in the micrometer range, and the fluidic device for use in the method of the first aspect of the invention may therefore be referred to as a microfluidic device.

The present invention also provides the microfluidic device as described herein. The use of microfluidic channels to hold the first, second, third and fourth fluid flows ensures that the flows take place at low Reynolds numbers. Under the diffusive separation steps described herein, convection and diffusion are the only relevant mechanisms of mass transport within the system. Accordingly, this allows accurate numerical calculations to be performed for each component of a given size, as described in further detail herein. Where electrophoretic methods are used for separation, convection and electrophoresis are the only relevant mechanisms of mass transport within the system.

The separation channels have suitable dimensions allowing for the generation and maintenance of a laminar flow of two (or three) streams within. The laminar flow of two streams means that the flows are side by side and are stable. Thus, there are typically no regions where the fluids recirculate, and the turbulence is minimal. Typically such conditions are provided by small channels, such as microchannels.

The general dimensions of the channels in the device are selected to provide reasonable mobilisation rates and analysis times. The dimensions of the device may also be selected to reduce the amount of fluid required for a sufficient analysis run.

Devices for use in the diffusion of a component across fluid flows, such as for use in dispersive measurements, are well known in the art, and are described, for example, by Kamholz et al. (*Biophysical Journal* 80(4):1967-1972, 2001).

Devices for use in the electrophoresis of a component across fluid flows are well known in the art, and are described, for example, by Herling et al. (*Applied Physics Letters* 102, 184102-4 (2013)). Thus, a separation channel may be provided with electrodes alongside the channel length for deflecting (distributing) charged components across the channel. This is distinguishable from the devices described by the Ramsey group, where electrodes are placed at the channel ends, in order to distribute components along the channel length.

A separation channel is a channel having suitable dimensions allowing for the generation of a stable fluid flow and for achieving an adequate separation of components across the flow. The first separation channel is the region where the first fluid flow is brought into contact with the second fluid flow. The second separation channel is the region where the third fluid flow is brought into contact with the fourth fluid flow.

A reference to a separation channel herein is a reference to a channel having a substantially rectangular cross section. Thus, the separation channel may be formed of a substantially flat base with walls which extend substantially vertically therefrom, and optionally a top cover. Typically, the base and the walls are formed into a silicone substrate. The cover may be a glass cover, for example a standard glass slide or a borosilicate wafer.

Typically, other channels within the device, such as a supply channel, are also substantially rectangular.

The first separation channel is in fluid communication with one or more reservoirs for the supply of first fluid. The first separation channel is in fluid communication with one or more reservoirs for the supply of second fluid.

The second separation channel is in fluid communication with one or more reservoirs for the supply of fourth fluid. The second separation channel is in fluid communication with the first separation channel via the first flow separator for the supply of a third fluid.

The separation channel has a region having a substantially constant width throughout its length. The width of this region in the separation channel may be at most 500 at most 700 at most 1,000 IJm" at most 2,000 or at most 5,000 The width of this region may be at least 5 at least 10 at least 50 at least 100 or at least 200 In one embodiment, the width of this region in the separation channel may be in a range selected from the upper and lower values given above. For example, the width may be in the range 10 to 500

In one embodiment, a separation channel has an upstream region that is a large section channel and a downstream region that is a small cross section channel. The region of the channel discussed above may be the small cross section region of the channel.

The large section channel may be the region where the flow of a component solution (such as the first flow) is brought into contact with the flow of a blank solution (such as the second flow). The flows are then directed by the large cross section channel to the small cross section channel. It is in the small cross section channel that the lateral movement of the one or more components into the blank flow is monitored. The large cross section channel is in fluid communication with the small cross section channel.

The maximum width, W, of the large cross section channel is greater than the width of the small section channel. In one embodiment there is no section in the large cross section channel that is of a width smaller than the width of the small cross section channel. In one embodiment the minimum width of the large cross section channel is the same as the width of the small cross section channel.

The maximum width, W, of the large section channel may be at most 500 at most 700 at most 1,000 at most 2,000 at most 5,000 or at most 10,000 Generally channel widths of greater than 10,000 are not practical, as the material from which the device is made, typically PDMS, is likely to sag. The maximum width, W, of the large section channel may be at least 50 at least 100 at least 200 or at least 500 In one embodiment, the maximum width of the large cross section channel may be in a range selected from the upper and lower values given above. For example, the width may be in the range 200 to 5,000 such as 200 to 1,000 or such as 1,000 to 5,000

The length of the large section channel is at most 500 at most 700 or at most 1,000 The length of the large section channel is at least 10 at least 50 at least 100 or at least 200 In one embodiment, the length of the large cross section channel may be in a range selected from the upper and lower values given above. For example, the length may be in the range 50 to 500 such as 100 to 500.

A large cross section channel limits the effects of stagnation at the junction of supply channels in a fluid device. Thus, for example, a calculated diffusion coefficient value, and the hydrophobic radius, may be considered as having greater accuracy where a large cross section channel is used at the fluid junction.

Where the large cross section channel comprises a region of substantially constant maximum width and a downstream region where the width converges to the width of the small cross section channel, the region of substantially constant maximum width may be at least 50%, at least 60%, at least 70%, at least 80% or at least 90% of the total length of the large cross section channel.

The length of channel region having a substantially constant width is sufficient to allow components of interest to move into a contact fluid flow at typical fluidic flow rates. Channel lengths of 1 mm length or more are generally sufficient. In one embodiment, the channel region having a substantially constant width is at least 0.5 mm, at least 1 mm, at least 2 mm, or at least 5 mm long. In one embodiment, the channel region having a substantially constant width is at most 10 mm, at most 20 mm, at most 50 mm, at most 100 mm or at most 500 mm long. In one embodiment, the channel region having a substantially constant width may be in a range selected from the upper and lower values given above. For example, the channel region having a substantially constant width may be in the range 0.5 to 50 mm, such as 1 to 20 mm.

The flow of the fluids is along the longitudinal axis of the small cross section channel. The diffusion of components in the component flow into the blank flow is transverse to the longitudinal axis of flow, across the width of the channel.

Typically the flow apparatus comprises a first supply channel and a second supply channel, which channels are in fluid communication with the downstream first separation channel. The first supply channel is for holding the first fluid flow and the second supply channel is for providing the second fluid flow. The first and second supply channels meet at a junction with the downstream separation channel, which is adapted to hold the first and second fluid flows in a laminar flow. The channels provide fluid communication between the reservoirs and the separation channel.

Similarly, the flow apparatus comprises a fourth supply channel, which channel is in fluid communication with the downstream second separation channel. The fourth supply channel is for holding the fourth fluid flow. The fourth supply channel meets with a third supply channel at a junction with the downstream second separation channel, which is adapted to hold the third and fourth fluid flows, such as in a laminar flow. The channels provide fluid communication between the reservoirs and the second separation channel. The third supply channel is the channel downstream of the first flow separator.

In one embodiment, a separation channel comprises a first large cross section channel and a second small cross section channel that is downstream and in fluid communication with the large cross section channel.

The present inventors have found that the use of a large cross section channel at the junction where the fluids, such as the first and second fluids or the third and fourth fluids, first contact minimises fluid stagnation. Such channels are described in PCT/GB2013/052757.

The flow of fluids is along the longitudinal axis of the separation channel. The movement of a component or components from the one flow into another flow, such as the diffusion of the component or components, is transverse to the longitudinal axis of flow, across the width of the channel. The flow apparatus of the present invention may incorporate the flow device of the inventors' earlier work, as described in PCT/GB2013/052757, the contents of which are hereby incorporated by reference in their entirety.

The flow apparatus includes a first flow separator downstream from and in fluid communication with the first separation channel. The first flow separator is a channel that is located across a part of the separation channel to collect a part of the laminar flow, and in particular to collect a part of the first fluid flow, a part of the second fluid flow or parts of the first and second fluid flows. The location and the width of the channel are selected depending upon the part of the laminar flow that is to be collected and the proportion of the flow that is to be collected.

The flow separator diverts a part of the flow from the separation channel. The flow separator provides the diverted flow to, and is in fluid communication with, a downstream second separation channel. A first separation channel is provided upstream of a second separation channel. The first separation channel is in fluid communication with first and second supply channels. The first channel is for supply of a first fluid containing the component, and the second channel is for supply of a second fluid which is a blank fluid. The first and second flows are brought together at a junction at the upstream end of the first separation channel.

A first flow separator is provided at the downstream end of the first separation channel. The first flow separator collects a part of the fluid flow from the first separation channel and diverts this flow to the downstream second separation channel, for example via a third fluid supply channel which is in fluid communication between the first flow separator and the second separation channel. The collected part from the first separation channel is the third fluid flow.

The second separation channel is in fluid communication with the upstream first flow separator and a fourth supply channel. The fourth supply channel is for supply of a fourth fluid which is a blank fluid. The third and fourth fluid flows are brought together at a junction at the upstream end of the second separation channel.

Optionally, a second flow separator is provided at the downstream end of the second separation channel. The second flow separator collects a part of the fluid flow from the second separation channel. The collected part from the second separation channel is the fifth fluid flow. This diverted flow may be collected.

The devices of the invention may be prepared in part using standard photolithographic techniques, such as described herein.

The channel surfaces of the fluid device may be adapted to prevent components from adhering to the surfaces. Thus, in one embodiment, the channel surfaces limit or prevent absorption of a component onto the surface.

In one embodiment, the channels within the fluidic device are hydrophilic or hydrophobic. The present inventors have found that the use of hydrophilic channel surfaces, particularly in the detection zone, prevent the absorption of hydrophobic components, such as hydrophobic proteins, thereby improving the analysis of components in the device. Similarly, hydrophobic channels may be used to prevent the absorption of hydrophilic components.

In particular the inventors have found that the use of hydrophilic or hydrophobic channel surfaces is beneficial at the stage of labeling and denaturing the component. The amount of insoluble material that is generated in the labeling step is minimised.

Hydrophilic channels may be prepared using techniques familiar to those in the art. For example, where the channels in a device are prepared from PDMS, the material may be plasma treated to render the surfaces hydrophilic. Here, the plasma treatment generates hydrophilic silanol groups on the surface of the channels. Such techniques described by Tan et al. (*Biomicrofluidics* 4, 032204 (2010).

The flow device of the present invention may include further separation channels that are arranged in series downstream from the second separation channel. Thus a part of the fluid flow in the second separation channel may be diverted, and that separated flow, the fifth fluid flow, may pass into a third separation channel where it is contacted with a sixth fluid flow. Component present in the fifth fluid flow may be permitted to move into the third fluid flow to achieve a non-uniform distribution across fifth and sixth fluid flows.

A downstream end of the flow apparatus may be provided with a dry mass detector.

Other Preferences

Each and every compatible combination of the embodiments described above is explicitly disclosed herein, as if each and every combination was individually and explicitly recited. Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental

Device Fabrication and Operation

Devices were fabricated to a channel height of 25 through a soft-lithography approach using SU8-3025 photoresist (MicroChem, Newton Mass., USA) spun at 3000 rpm. The illuminated and developed resist forms a negative mould onto which uncrosslinked polydimethylsiloxane (PDMS, Sylgard 184, Dow Corning, Midland Mich., USA) was poured and cured. Pealing of the hardened PDMS and plasma bonding it to a microscope glass slide resulted in sealed microchannels accessible with elastic tubing through holes punched into the cured POMS. The electrodes were generated by placing the bonded devices on a hotplate at 78° C. and inserting a low melting-point alloy (51% In, 32.5% Si, 16.5% Sn, Indium Corporation, Utica N.Y., USA) into a self-aligned mould. A series of pillars with radius 25 and separated by 25 retained the molten metal due to its surface tension, and upon reducing the temperature, the alloy solidified and formed solid wall electrodes.

The design of the present device is shown in FIG. 1 and comprises a first module for electrophoretic separation (1) and a module for diffusion separation (2). The first module allows the size-over-charge ratio of a component to be determined, and the second module allows the size of a component to be determined.

Fluid handling was effected by withdrawing liquid from the common outlet with a syringe pump (neMESYS, Cetoni GmbH, Korbussen, Germany) at a constant flow rate of 250 IJUh and attaching reservoirs to all inlets (gel loading pipet tips, FisherBrand, Fisher Scientific, Loughborough, UK). The hydrodynamic resistor network on the device results in a flow of around 125 IJUh through both the free flow electrophoresis and the diffusion modules. The flow ratio between analyte solution and auxiliary fluids (buffer flows) was 1:10 for both the first and second modules.

Description and Use of a Fluid Device

FIG. 1 is a schematic of a fluidic device 3 according to one embodiment of the invention. Such a fluid device was used in the exemplary methods described herein.

The device includes an electrophoretic separation unit 1 and a diffusion separation unit 2. The device is prepared using standard soft-lithographic techniques, as described above. Additionally, methods for the preparation of diffusion devices and electrophoretic devices are described by Kamholz et al. (*Biophysical Journal* 80(4):1967-1972, 2001) and Herling et al. (*Applied Physics Letters* 102, 184102-4 (2013)), and the methods described therein may be adapted for use in the preparation of the device described herein.

The device 3 includes a first separation channel 4 within the electrophoretic separation unit 1. Electrodes 5 are provided either side of the channel, along its length. The electrodes 5 are connected to a suitable power supply (not shown) for applying a field across the separation channel 4. The first separation channel 4 is provided for the electrophoretic distribution of components. The first separation channel 4 is supplied by an upstream first supply channel 6 and upstream second supply channels 7. The first supply channel 6 is for supplying a first fluid flow to the first separation channel 4 from a first fluid reservoir 8 ("Sample inlet"). The first fluid flow comprises a component, for example in a multicomponent mixture. The second supply channels 7 are for supplying second fluid flows to the first separation channel 4 from a second fluid reservoir 9 ("Buffer inlet"). In use, first and second fluids are permitted to flow from the reservoirs 8 and 9 through the supply channels 6 and 7 to meet at a junction 10 at the upstream end of the first separation channel 4. The second fluid flows are provided either side of the first fluid flow. The first separation channel 4 has an upstream region of large cross section and a downstream region of small cross section. The presence of a large cross section channel at the upstream region of a separation channel is associated is with the formation of a stable fluid flow in the separation channel.

The movement of fluids through the device may be controlled by syringe pumps (not shown). These may be located at the upstream end to individually control the flow of fluid from each reservoir. Attentively, a pump may be located at a downstream end to draw material through the apparatus. Fluid may also move through the device under a gravity feed.

Contacting first and second fluid flows are permitted to flow through the first separation channel. An electric field is applied across the first separation channel 4 by appropriate application of a voltage across the electrodes 5. The applied electric field may cause components to move from the first fluid flow into one of the second fluid flows, based on the charge to size ratio of that component. The movement of a component in response to an applied field may be referred to as deflection. At the downstream end of the first separation channel 4 a component or components are non-uniformly distributed across the first and second fluid flows.

The direction of the component movement across the channel is dictated by the charge of the component. Positively-charged components will move towards a negative electrode, whilst negatively-charged components will move towards a positive electrode. For this reason two second fluid flows are provided either side of the first fluid flow: each of the second fluid flows will revive either positively- or negatively-charged components.

The degree of deflection will depend on the mass-charge ratio of a component. Components having a large charge and/or smaller mass will be deflected more than those component having a small charge and/or large mass. Components that are deflected more will have the greatest movement from the first fluid flow, and will located closer to the boundary of the second fluid flow With the channel wall. Components that are deflected least will have the least movement from the first fluid flow, and will located closer to the contact region of the second fluid flow with the first fluid flow.

Figure 2:
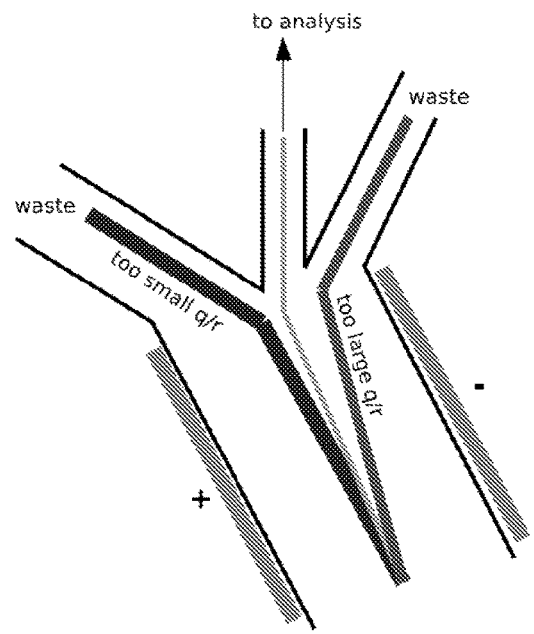
FIG. 2 is a schematic of a flow separator of a flow apparatus according to one embodiment of the invention. The flow separator is for separating a part of fluid flow at a downstream end of a separation channel where components are distributed by electrophoresis. The flow separator collects a part of fluid flow containing a component having a particular mass to charge ratio, and that separator may supply a downstream distribution channel, such as shown in the flow apparatus of FIG. 1. Components having different mass to charge ratios are diverted elsewhere.

At the downstream end of the first separation channel 4 there is provided a first fluid separator 11 for diverting a part of the fluid flow from the first separation channel 4. The first flow separator 11 is located to collect a part of the cross section of the contacting first and second fluid flows containing a component of interest. The diverted part of the fluid flow is a third fluid flow containing a component. The flow separator diverts a part of the first and/or second fluid flow into a third supply channel. The diversion step allows for the separation of a component or components having a particular mass-charge ratio from components having alternative mass-charge ratios. In this way the diversion step may be used to at least partially purify a component from other components in a multicomponent mixture. The principle is shown in FIG. 2 where a central flow separator diverts components having a charge to size ratio of interest, and those components with ratios too high or too low are diverted elsewhere.

Also, the diversion step may be used to analyse a component or components. Only those components have a particular mass-charge ratio will be diverted. Thus, the presence of a component in the third supply channel (or downstream of that channel) is indicative of the component having a particular mass-charge ratio.

The remaining parts of the fluid flow are also diverted and the flows are later recombined in a collection chamber 12 at the downstream outlet of the device. Alternatively these diverted parts may also be subsequently analysed using diffusive techniques, such as described below for the diverted third fluid flow.

The first flow separator supplies a downstream third supply channel 13 ("Sample loop") which in turn supplies a second separation channel 14.

The second separation channel 14 is supplied by the upstream third supply channel 13 and upstream fourth supply channels 15. The fourth supply channels 15 are for supplying fourth fluid flows to the second separation channel 14 from a fourth fluid reservoirs 16 ("Buffer inlets"). In use, third and fourth fluids are permitted to flow from the first flow separator 11 and the fourth fluid reservoirs 16 through the supply channels 13 and 15 to meet at a junction 16 at the upstream end of the second separation channel 14. The fourth fluid flows are provided either side of the third fluid flow. The second separation channel 14 has an upstream region of large cross section and a downstream region of small cross section. The presence of a large cross section channel at the upstream region of a separation channel is associated with the formation of a stable fluid flow in the separation channel.

Contacting third and fourth fluid flows are permitted to flow through the second separation channel 14. Components in the third fluid flow are permitted to diffuse from the third flow into the fourth flows as the flow passes along the second separation channel 14. The amount of movement is related to the size of the component. At the downstream end of the second separation channel 14 a component or components are non-uniformly distributed across the third and fourth fluid flows.

The amount of movement will depend on the size of a component. Components having a large size will move less than those components having a small size. Small components will have the greatest movement from the third fluid flow. Large components will have the least movement from the first fluid flow, and may remain substantially with the third fluid flow.

The diffusion of components may be measured at different diffusion times. In practice the diffusion profile of components across the second separation channel 14 may be measured at different locations along the channel. This is described in the worked examples in the present case.

The measurement of the diffusion profile at different diffusion times may be achieved at a single location in the second separation channel 14 with a change in the flow rates through the system. This is less preferred as changes in flow rate will require changes to the separation conditions in the first separation channel 4 to ensure that the same components are collected at the send of the first separation channel. For example, with a change in the flow rate through the system it may be necessary to also change the applied field across the first separation channel 4.

Components

Protein solutions were prepared at a concentration of 2 mg/mL in 5 mM HEPES buffer at pH 8.0. Covalent labeling was effected by adding 600 of a latent fluorophore (or-thophthalaldehyde, P0657, Sigma Aldrich, Dorset, England) and 900 2-mercaptoethanol (35602, Thermo Scientific, Cramlington, UK). The labeled samples were incubated for at least 5 min on ice (+4° C.) before use in the devices. The labeled protein solutions were then supplemented with 20% v/v dimethyl sulfoxide to avoid mutual adhesion of the proteins.

A buffer solution of 5 mM HEPES at pH 8.0, supplemented with 20% v/v dimethyl sulfoxide, was used as an auxiliary fluid.

The fluorescent colloids used for sizing of a mixture were obtained from FluoroMax (G50 and G200) and their radii were determined by the manufacturer to be 23.5 and 100 nm, respectively.

Data Analysis

In principle, diffusive sizing was achieved as described in the patent application by the present inventors in PCT/GB2013/052757. Thus, so-called basis functions $B_r(y)$ are generated by propagating a large number of individual particles of a given size r through the channel via convection and diffusion. The experimental profiles at different positions in the diffusion module are then fitted to a linear combination of these basis functions to obtain coefficients $c_r$ quantifying the proportion of particles with radius r in the solution. The optimisation algorithm itself is implemented by a basin hopping procedure with at least 100 random displacements to find the global minimum of the residuals including a least-entropy term.

The inclusion of an electrophoretic separation step adds charge as an independent variable. Now, the basis functions additionally have an amplitude corresponding to the fraction of analyte that is transferred to the sizing module according to the size-over-charge ratio for a given magnitude of the electric field. This is simulated by propagating particles with radius r through the electrophoresis module and shifting the position of the centre of the obtained distribution proportionally to the migration velocity. The amplitude of the basis function denoted by $B_{r,q}(y)$ was then determined by counting the fraction of particles in the relevant region at the outlet of the separation module. By tuning the electric field, this fraction is altered and a complete set of diffusion measurements at different voltages can be determined, which can be analysed globally, i.e., the linear combination of basis functions must now satisfy the diffusion profiles obtained for all applied voltages. This multiplicatively increases the resolution of the method since particles with similar size can still be pre-separated according to charge which leads to a different amplitude signature when changing the electric field.

In the global analysis of the inventors earlier work in PCT/GB2013/052757 a global analysis of components came from looking at diffusion profiles at multiple diffusion time locations, for example at multiple locations along a single separation channel. The diffusion profiles all relate to the same physical parameter (hydrodynamic radius [size]), and increasing the number of measured diffusion profiles at different diffusion times may help up to a certain point in resolving a complex mixture of components. In the present case, by including an additional separation step prior to a diffusional separation, and one which is based on parameters that are independent of the hydrodynamic radius such as charge and isoelectric point, for example, the amount of information contained in the set of profiles is increased multiplicatively for each and every separation parameter (for example where those parameters are independent).

Use of Device

Figure 3:
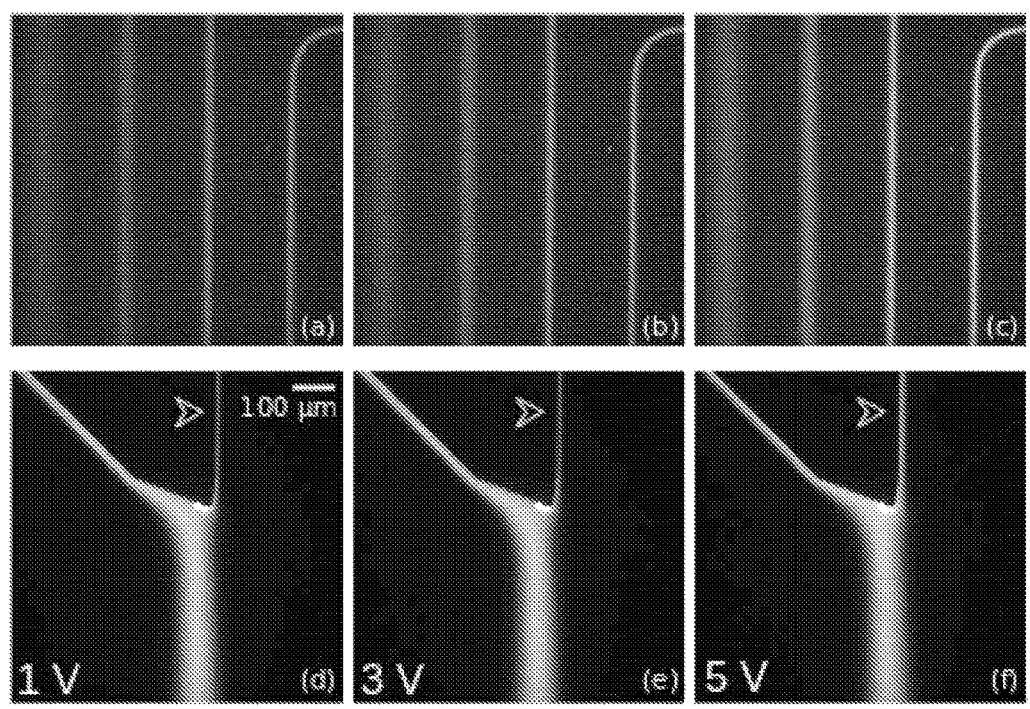
FIG. 3 is a series of fluorescence images taken at (a) to (c) the diffusion separation channel of a device having the design shown in FIG. 1; and (d) to (f) the flow separator at the downstream end of the electrophoresis separation channel of a device having the design shown in FIG. 1, where the images (a) and (d) are taken with a 1 V applied field across the electrophoresis separation channel; (b) and (e) a 3 V applied field; and (c) and (f) a 5V applied field. The yellow arrowheads point to the diverted part of the fluid flow that is subsequently supplied to a downstream diffusive separation channel. The component used is l3-lactoglobulin at a concentration of 2 mg/mL.
Figure 4:
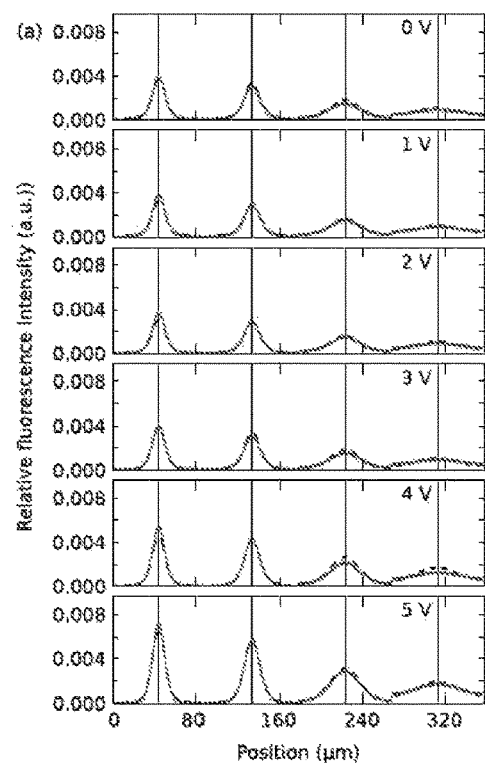
FIG. 4 (a) shows the diffusion profiles, as measured by change in relative fluorescence intensity with channel position recorded for I3-lactoglobulin at 4 positions (2.5, 4.7, 20.7 and 64.7 mm, from left to right) in the diffusive separation channel of a device having the design shown in FIG. 1; and (b) shows the change in relative fluorescence intensity with change in component charge (e) and component size (nm), as determined from the experimentally measured size and charge properties from the experiments.
Figure 4:
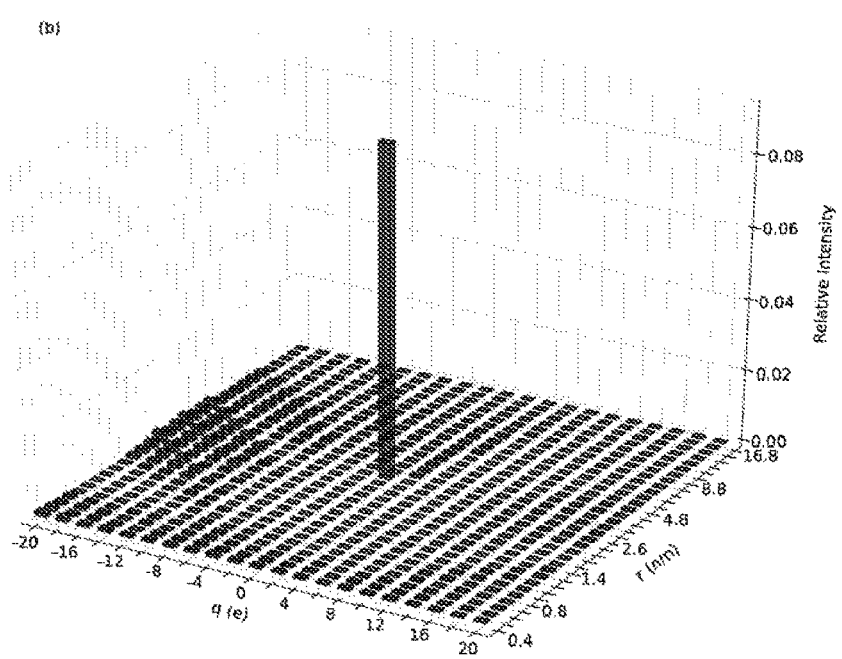

A set of fluorescence microscopy images inside the diffusion channel and at the end of the electrophoresis module are presented in FIG. 3. Stepwise increase of the applied voltage from 1 V to 5 V deflects the analyte beam—here consisting of 13-lactoglobulin at a concentration of 2 mg/mL labeled with a latent fluorophore—towards the outlet for the analysis chamber (marked with yellow arrowheads) and consequently increases the amplitude of the profiles inside the diffusion module. From these images, the fluorescence profiles at four positions in the diffusion channel (at 2.5,4.7, 20.7, and 64.7 mm downstream from the nozzle) can be extracted. Profiles obtained for 2 mg/mL 13-lactoglobulin, dissolved in 20% DMSO and labeled with a latent fluorophore (OPA) for voltages ranging from 0 V to 5 V are shown by the dashed black lines in FIG. 4(a). The red lines are a global fit to these data resulting in the basis-function coefficients depicted FIG. 4(b). This set of coefficients reveals that we can simultaneously determine size and charge of analytes. The obtained hydrodynamic radius of around 3 nm corresponds well to our previous findings. However, at this stage, the value for the charge is not yet reliable since the selectivity of the separation module is still moderate.

Figure 5:
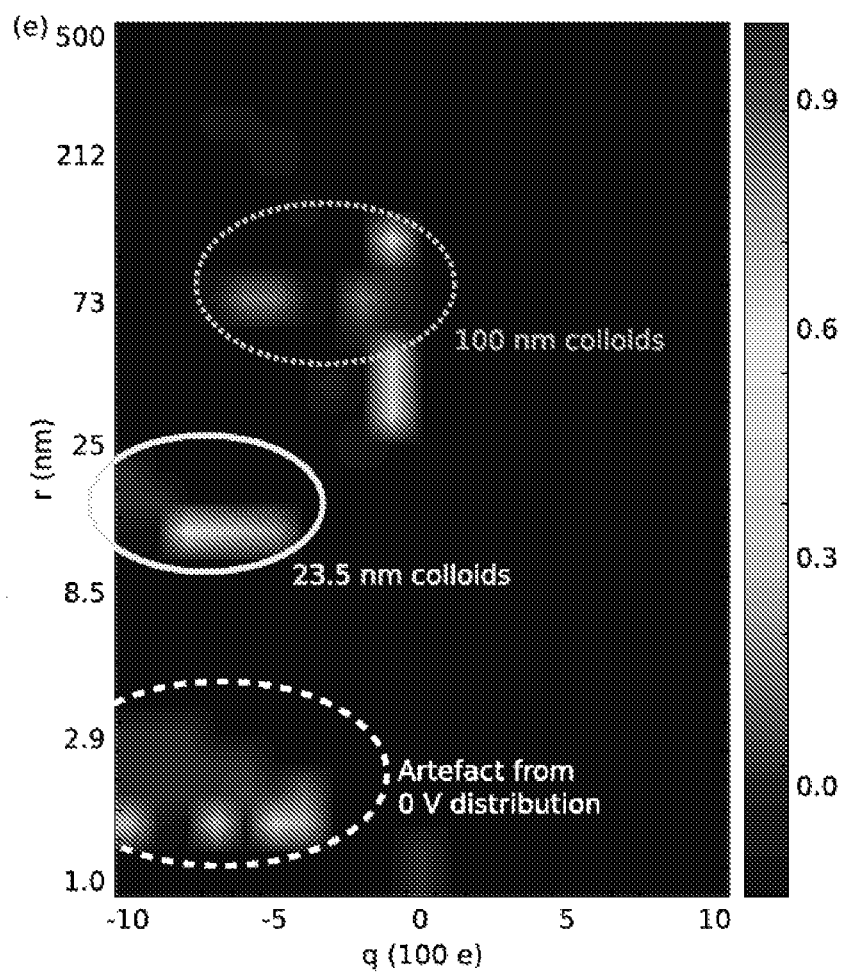
FIG. 5 (a) to (c) are a series of fluorescence images taken at the flow separator at the downstream end of the electrophoresis separation channel of a device having the design shown in FIG. 1, for the distribution of a mixture of fluorescent colloids with a nominal radius of 23.5 and 100 nm, where the images (a) is taken with a 0 V applied field across the electrophoresis separation channel; (b) a 0.9 V applied field; and (c) a 1.5 V applied field; (d) shows the diffusion profiles, as measured by change in relative fluorescence intensity with channel position recorded for fluorescent colloids at 4 positions (2.5, 4.7, 20.7 and 64.7 mm, from left to right) in the diffusive separation channel of a device having the design shown in FIG. 1; and (e) is the distribution density map for the analysed mixture of components showing the relative intensity of components measured for a particular combination of size, r (nm) and charge, 9 (100 e). The relative intensity shown by shading. The intensity map reveal a population corresponding to 100 nm colloids and 23.5 nm colloids in the original population of components.

To demonstrate the ability of separating and analysing mixtures, a solution of fluorescent colloids with radii of 23.5 and 100 nm was studied. FIGS. 5(a)-(c) show the fluorescence microscopy image of this mixture at the end of the electrophoretic separation module at voltages of 0, 0.9 and 1.5 V. In the absence of an electric field only a small fraction of the colloids is fed into the analysis channel. Importantly, only the smaller colloids are able to reach this channel by diffusion, which is visualised by the dotted red and dashed yellow guide to the eye lines revealing the diffusive spread of the 23.5 and 100 nm colloids, respectively. At non-zero fields more and more particles get defected into the analysis channel, and at 1.5 V (see FIG. 5(c)) both components of the mixtures reach the sizing module. Furthermore, at this voltage, the centre of the two colloid streams is now offset to each other as a result of their apparently distinct size-over-charge ratio.

In FIG. 5(d) the measured diffusion profiles inside the sizing module are shown in dashed black lines, whereas the corresponding fit is depicted in solid red lines. As already visible from the images at the end of the separation module, the amount of particles deflected into the sizing module increases strongly for higher voltages. Except for at zero field where according to the simulations only very small particles should reach the analysis channel, the fitted distribution describes the experiment very well, and the resulting coefficients presented in FIG. 5(e) reveal the presence of both the 23.5 and the 100 nm colloids. Additionally, the fit also includes a range of small particles that appear due to the colloids inside the sizing module at 0 V, where diffusion was not expected to allow the particles to enter the analysis channel yet. In order to avoid these artefacts, the device geometry can be altered to i) allow for a lesser relative amount of diffusion inside the separation module (for instance, by widening the channel), ii) increase the flow through the left waste channel to reduce the amount of analyte able to reach the sizing module at zero field, and iii) lead to a simpler flow field at the node connecting the separation and analysis/waste channels which would permit more accurate simulations.

In conclusion diffusional sizing after a separative electrophoretic step under steady-state laminar flow is demonstrated as a proof-of-principle experiment for multidimensional analysis of complex mixtures. The inventors have presented both accurate sizing of monodisperse solutions as well as of a mixture, where the electric field inside the separation channel was shown to alter the relative amounts of constituents of the mixture entering the analysis module. The limited resolution in the charge dimension originates from the present geometry of the electrophoretic module and is by no means fundamental to the approach. Indeed, the inventors have previously achieved charge measurements with an accuracy better than the charge of an electron.

REFERENCES

All documents mentioned in this specification are incorporated herein by reference in their entirety. GB 1320146.2 Hatch et al. *Nature Biotechnology,* 19(5):461-465, 2001 Herling et al. *Applied Physics Letters* 102, 184102-4 (2013) Jacobson et al. *Anal. Chem.* 1994,66,4127 Jacobson et al. *Anal. Chem.* 1994, 66, 3472 Kamholz et al. *Biophysical Journal* 80(4):1967-1972, 2001) Kamholz and Yager. *Biophysical Journal,* 80(1):155-160,2001. Kohlheyer et al. *Electrophoresis* 29, 977 (2008) Liu et al. *Anal. Chem.* 2000, 72, 4608 McDonald et al. *Ace. Chem. Res.* 35, 491 (2002) PCTfGB2013/052757 Tan et al. *Biomicrofluidics* 4, 032204 (2010) US 2006/263903 Wales et al. J. *Phys. Chem.* A 101, 5111 (1997)

The invention claimed is:
1. A method for analyzing a component, the method comprising the steps of:
   (i) providing the component in a first fluid flow;
   (ii) contacting the first fluid flow with a second fluid flow to generate a laminar flow,
   (iii) providing electrophoretic or thermophoretic movement of the component into the second fluid flow;
   (iv) diverting a part of the first fluid flow, a part of the second fluid flow, or parts of the first fluid flow and the second fluid flow, wherein the diverted part is a third fluid flow which comprises the component;
   (v) contacting the third fluid flow with a fourth fluid flow to generate a laminar flow;
   (vi) providing diffusion of the component into the fourth fluid flow;
   (vii) quantitatively determining a value of a first chemical or physical property of the component based on the electrophoretic or thermophoretic movement of the component into the second fluid flow; and

(viii) quantitatively determining a value of a second chemical or physical property of the component based on the diffusion of the component into the fourth fluid flow.

2. The method according to claim 1, further comprising the step of:
(ix) diverting a part of the third fluid flow, a part of the fourth fluid flow, or parts of the third fluid flow and fourth fluid flow, wherein the diverted part is a fifth fluid flow which comprises the component.

3. The method of claim 2, further comprising the subsequent steps of:
(xi) contacting the fifth fluid flow with a sixth fluid flow to form a laminar flow; and
(xii) providing a distribution of the component across contacting fifth and sixth fluid flows.

4. The method of claim 3, further comprising the subsequent step of:
(xiii) diverting a part of the fifth fluid flow, a part of the sixth fluid flow, or parts of the fifth fluid flow and sixth fluid flow; wherein the diverted part is a seventh fluid flow which comprises the component.

5. The method according to claim 2, further comprising the step of:
(x) subsequently labeling the component in the third fluid flow or the fifth fluid flow.

6. The method of claim 1, wherein step (iii) comprises the electrophoretic movement of the component into the second fluid flow.

7. The method according to claim 6, wherein the electrophoretic movement comprises isoelectric focusing.

8. The method according to claim 1, wherein the component has a hydrodynamic radius in the range of 0.5 nm to 200 nm.

9. The method according to claim 1, wherein the component has a hydrodynamic radius in the range of 0.5 nm to 25 nm.

10. The method according to claim 1, wherein the second chemical or physical property of the component is a diffusion coefficient of the component.

11. The method according to claim 1, wherein the second chemical or physical property of the component is a hydrodynamic radius of the component.

12. The method according to claim 1, wherein the first chemical or physical property of the component is a charge-to-size ratio of the component.

13. The method according to claim 1, wherein the first chemical or physical property of the component is an isoelectric point of the component.

14. The method according to claim 1, wherein the first chemical or physical property of the component is an ionic mobility of the component.

15. The method according to claim 1, wherein the first chemical or physical property of the component is the charge of the component.

16. The method according to claim 1, wherein the second chemical or physical property of the component the property of the component is the mass of the component.

17. The method according to claim 1, wherein quantitatively determining the value of the first chemical or physical property of the component and/or the quantitatively determining the value of the second chemical or physical property of the component comprises fitting an experimental diffusion profile of the component to a linear combination of basis functions.

18. The method according to claim 1, wherein the first fluid further comprises a second component having a value of the first chemical or physical property different from the value of the first chemical or physical property of the first component, and further comprising determining the value of the first chemical or physical property of the second component.

19. The method according to claim 18, wherein the second component has a value of the second chemical or physical property different from the value of the second chemical or physical property of the first component, and further comprising determining the value of the second chemical or physical property of the second component.

20. A flow apparatus for analyzing a component, the apparatus comprising:
a first separation channel for first and second flows in contact, wherein the separation channel is adapted to permit lateral movement of components between contacting first and second flows;
a first flow separator, in fluid communication with and downstream of the first separation channel, the first flow separator being adapted to divert a part of the first fluid flow, a part of the second fluid flow, or parts of the first fluid flow and the second fluid flow, from the first separation channel, the diverted flow being a third flow;
a second separation channel, in fluid communication with and downstream of the first flow separator, the second separation channel being for third and fourth flows in contact, wherein the separation channel is adapted to permit lateral movement of components between contacting third and fourth flows;
wherein the apparatus further comprises a second flow separator, in fluid communication with and downstream of the second separation channel, the second flow separator being adapted to divert a part of the third fluid flow, a part of the fourth fluid flow, or parts of the third fluid flow and the fourth fluid flow, from the second separation channel, the diverted flow being a fifth flow; and
a reagent flow channel for introducing a reagent to a component in the fifth diverted flow, wherein the reagent is a label or is capable of generating a detectable label upon reaction,
wherein the flow apparatus is configured for quantitatively determining a value of a first chemical or physical property of the component based on the electrophoretic or thermophoretic movement of the component into the second fluid flow, and
wherein the flow apparatus is configured for quantitatively determining a value of a second chemical or physical property of the component based on the diffusion of the component into the fourth fluid flow.

21. The flow apparatus of claim 20, wherein the apparatus further comprises a third separation channel, in fluid communication with and downstream of the second flow separator, the third separation channel being for fifth and sixth flows in contact, wherein the separation channel is adapted to permit lateral movement of components between contacting fifth and sixth flows.

22. The flow apparatus of claim 20, wherein the apparatus further comprises an analysis zone which is downstream of and in fluid communication with a flow separator.

23. The method according to claim 22, wherein the flow separator upstream of and in fluidic communication with the analysis zone is the second flow separator.

24. The flow apparatus according to claim 20, wherein at least one of the first and second separation channels is provided with electrodes along the channel length.

* * * * *